United States Patent [19]

Gerzon et al.

[11] Patent Number: 5,510,500

[45] Date of Patent: Apr. 23, 1996

[54] DERIVATIVES OF RYANODINE AND DEHYDRORYANODINE

[75] Inventors: Koert Gerzon; Rod A. Humerickhouse; Henry R. Besch, Jr.; Keshore R. Bidasee, all of Indianapolis, Ind.

[73] Assignee: Indiana University Foundation, Bloomington, Ind.

[21] Appl. No.: 443,273

[22] Filed: May 17, 1995

Related U.S. Application Data

[60] Division of Ser. No. 25,150, Mar. 2, 1993, Pat. No. 5,432, 288, which is a continuation-in-part of Ser. No. 857,622, Mar. 25, 1992, abandoned, which is a continuation-in-part of Ser. No. 687,712, Apr. 18, 1991, abandoned.

[51] Int. Cl.$^6$ ................................................. C07C 25/02
[52] U.S. Cl. .................................................. 552/8
[58] Field of Search ...................................... 552/8

[56] References Cited

PUBLICATIONS

CA 120:290037k $O_{10}$–$O_{eq}$–N–. . . site. Bidasse et al., p. 1025, 1994.

*Primary Examiner*—Joseph K. McKane
*Attorney, Agent, or Firm*—Woodard, Emhardt, Naughton, Moriarty & McNett

[57] ABSTRACT

Novel $O_{10eq}$-derivatives of ryanodine and dehydroryanodine characterized as binding strongly to ryanodine receptor, useful in affecting $Ca^{++}$ efflux in tissue and also in isolating ryanodine receptor from sarcoplasmic reticulum. Also described are novel radio-iodinated alanine derivatives useful to radio label ryanodine and dehydroryanodine derivatives.

3 Claims, No Drawings

DERIVATIVES OF RYANODINE AND DEHYDRORYANODINE

This application is a division of application No. 08/025,150, filed Mar. 2, 1993, now U.S. Pat. No. 5,432,288, which is a continuation-in-part of U.S. patent application Ser. No. 07/857,622 filed Mar. 25, 1992, abandoned and hereby incorporated herein by reference, which is a continuation-in-part of U.S. patent application Ser. No. 07/687,712, filed Apr. 18, 1991, abandoned.

FIELD OF THE INVENTION

This invention relates to novel $O_{10equatorial}$ ($O_{10eq}$) ester derivatives of the alkaloids ryanodine and dehydroryanodine.

BACKGROUND OF THE INVENTION

Ryanodine and dehydroryanodine are represented by the following formula:

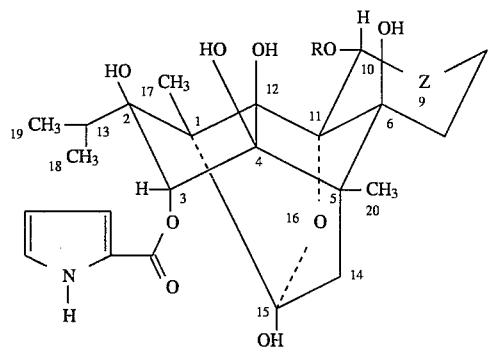

wherein, when R is H and Z is C(H)CH$_3$, ryanodine is represented, and when R is H and Z is C=CH$_2$, dehydroryanodine is represented.

Ryanodine (Merck Index number 8065-9th Edition) and dehydroryanodine are insecticidal alkaloids derived from the stem and roots of the plant *Ryania speciosa* Vahl, native to Trinidad. Crude extracts of the plant contain upwards of 25 alkaloids. Ryanodine is 700 times more potent as an insecticide than the crude alkaloidal extract, and was first isolated by Rogers et al, *J.Am Chem Soc.* 70 3086 (1948). Its structure was determined by Wiesner et al, *Tetrahedron Letters* 1967 221. The purification and structure of dehydroryanodine are disclosed in publications by Waterhouse et al, *J. Chem Soc. Chem. Commun.*, 1984 1265 and *J.Chem Soc., Perkin Trans* 2 1985 1011. A later paper by the same group published in *J. Med. Chem.*, 30 710 (1987), discloses a number of derivatives of ryanodine as well as three new alkaloids. Ruest et al, *Can. J. Chem.*, 63 2840 (1985) disclose a number of other *Ryania speciosa* alkaloids. The above publications disclose one derivatizate of the $10_{eq}$-hydroxyl, the acetate.

The pharmacology of ryanodine is summarized in an article by Jenden and Fairhurst, *Pharmacological Reviews* 21 1 (1969). In addition to its insecticidal properties, ryanodine also has a profound effect on mammalian skeletal muscle (irreversible confracture) and a negative inotropic effect on mammalian cardiac muscle. Jenden and Fairhurst conclude that ryanodine specifically interferes with vertebrate skeletal muscle relaxation, an activity believed to be effected by sequestration of Ca$^{++}$ ions by the sarcoplasmic reticulum. Ryanodine has been shown to obstruct active uptake of Ca$^{++}$ by skeletal muscle sarcoplasmic reticulum (SR). It therefore follows that ryanodine interferes with intracellular Ca$^{++}$ transport mechanisms and inhibits the normal lowering of the sarcoplasmic Ca$^{++}$ concentration that effects relaxation. In cardiac muscle, ryanodine's inhibition of SR Ca$^{++}$ uptake results in a depletion of SR Ca$^{++}$ stores with a subsequent loss of contractility. Ryanodine is also postulated to have other pharmacologic actions in smooth muscle and in systems free of functional remnants of the SR such as nervous and hepatic tissue. Here again, these effects are also Ca$^{++}$ dependent.

Specific information about the mode of action of ryanodine on cardiac SR was published by Sutko, Willerson, Besch et al *J.P.E.T.* 209 37 and Jones, Besch, Sutko et al id 40 (1979). More specific information is to be found in a paper by Inui et al, *J.B.C.* 262 15637 (1987). The authors found that ryanodine reacts with Ca$^{++}$ release channels localized in the terminal cisternae of the SR. The ryanodine receptor from cardiac SR used by the authors was purified by selective chromatography.

SUMMARY OF THE INVENTIONS

Preferred embodiments of this invention provide certain $10_{eq}$-ester derivatives of ryanodine and dehydroryanodine having the following formula:

Figure 2

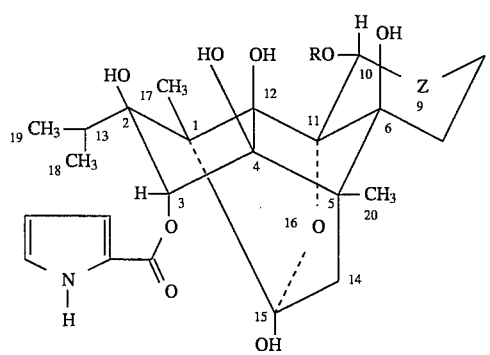

One preferred embodiment of the invention provides such $10_{eq}$-ester derivatives of ryanodine anddehydroryanodine in which Z is C(H)CH$_3$ or C=CH$_2$ and R is HOOC—CH$_2$CH$_2$—CO—, H$_3$CNHCO—CH$_2$—CH$_2$—CO— or R$^1$NH(CH$_2$)$_n$—CO—, wherein n is 1–3; and R$^1$ is H or a lipophilic group. Lipophilic groups of particular interest which R$^1$ represents include adamantanecarbonyl, adamantylmethylcarbonyl, adamantyl-1-oxycarbonyl, benzyloxycarbonyl, benzoyl, substituted benzoyl, phenylacetyl and the like. Other groups of interest which R$^1$ can represent include senecioyl, geranoyl, farnesoyl and the like lipophilic groups as well as N-biotinyl-β-alanyl, β-alanyl, and the like groups of biological interest. The term "substituted benzoyl" includes halo (chloro, bromo, and iodo), alkoxy (C$_{1-4}$ alkyloxy) including methoxy, ethoxy, n-butoxy, n-propoxy, isobutoxy and the like groups, azido, nitro, hydroxy and C$_{1-4}$ alkyl including methyl, ethyl, isopropyl,.n-butyl and the like groups. The substituents may be ortho, meta or para to the benzoyl carbonyl and there may be multiple substituents; ie., 5-azido-2-nitro,2,3-dimethoxy, 2,4 dichloro, 2-methyl-4-chloro, etc. Of the above substituted benzoyl derivatives, the iodo derivative is of particular interest because by employing radio-iodine, a tracer compound of great interest is produced, as will be delineated hereafter.

Compounds of this first preferred embodiment of the invention and coming within the scope of the formula of FIG. 2 include: benzoyl-β-alanyl-dehydroryanodine, 1-adamantanecarbonyl-β-alanyl-dehydroryanodine, 1-adamantanecarbonyl-γ-aminobutyryl-ryanodine, benzoyl-β-alanyl-ryanodine, benzoyl-γ-aminobutyryl-ryanodine, p-iodobenzoyl-β-alanyl-ryanodine, p-iodobenzoyl-β-alanyl-dehydroryanodine, p-ethoxybenzoyl-β-alanyl-ryanodine, phenylacetyl-glycyl-ryanodine, phenylacetyl-γ-aminobutyryl-ryanodine, 1-adamantylmethylcarbonyl-glycyl-ryanodine, 1-adamantylmethylcarbonyl-β-alanyl-dehydroryanodine, 1-adamantylmethylcarbonyl-γ-aminobutyryl-ryanodine, adamantyl-1-oxycarbonylglycyl-ryanodine, adamantyl-1-oxycarbonyl-β-alanyl-ryanodine, adamantyl-1-oxycarbonyl-γ-aminobutyryl-ryanodine, glycyl-ryanodine, β-alanyl-ryanodine and γ-aminobutyryl-ryanodine and the like compounds.

A second preferred embodiment of the invention provides such $10_{eq}$-ester derivatives of ryanodine and dehydroryanodine in which Z is C(H)CH$_3$ or C=CH$_2$ and R is R'—NH—C(=N—R')—NH—(CH$_2$)$_n$—CO' wherein R' is H or Cbz (carbobenzyloxy) and n is 1 or 2. Compounds represented by the above formula in which R' is Cbz are primarily intermediates useful in the production of the pharmacologically more active species, those compounds represented by the above formula in which R' is H.

Compounds of this second preferred embodiment and coming within the scope of the above formula include $O_{10eq}$-N,N'-bis-Cbz-guanidinoacetyl-ryanodine, $O_{10-eq}$-N,N'-bis-Cbz-guanidino-β-propionyl-ryanodine, $O_{10eq}$-N,N'-Cbz-guanidinoacetyl-dehydroryanodine, $O_{10eq}$-N,N'-bis-Cbz-guanidino-β-propionyl-dehydroryanodine, $O_{10eq}$-guanidinoacetyl-ryanodine, $O_{10eq}$-guanidino-β-propionyl-ryanodine, $O_{10eq}$-guanidinoacetyl-dehydroryanodine and $O_{10eq}$-guanidino-β-propionyl-dehydroryanodine.

The chief utility of the compounds of the first preferred embodiment of the invention wherein R is H$_3$CNHCO—CH$_2$CH$_2$—CO— or R$^1$ as defined with the proviso that n is only 2 when Z is C=CH$_2$ and of the second preferred embodiment, is a pharmacologic action—the ability of the compounds to affect the function of the junctional SR Ca$^{++}$-release channel of striated muscle. The effect of the parent compounds, ryanodine and dehydroryanodine, is complex; at low concentrations of drug (<μM), the Ca$^{++}$ release channel is opened thereby permitting an increased efflux of Ca$^{++}$, whereas at higher concentrations (>μM), the channel is closed, thereby interdicting Ca$^{++}$ efflux. Addition of the side chain at the $10_{eq}$-hydroxyl confers selectivity for the opening action of ryanodine. The compounds of this invention are also useful in affinity chromatography for isolating and purifying the Ryanodine receptor and in photoaffinity labeling of the same receptor and in preparing anti-ryanodine anti-bodies using Ryanodine protein-conjugates.

The compounds of the first and second preferred embodiments, because of their profound effects on Ca$^{++}$ ion movement within striated muscle, are potentially useful in the treatment of heart disease, particularly as anti-fibrillatory agents.

The preparation of compounds of the first embodiment can be briefly summarized as follows. Compounds of the first embodiment, wherein R$^1$ is benzyloxycarbonyl and n is 1–3, are prepared by direct acylation of the $10_{eq}$-hydroxyl of ryanodine or of dehydroryanodine. Hydrogenolysis of those derivatives in which Z is C(H)CH$_3$ yields the corresponding compounds wherein R$^1$ is H (the unsubstituted amino acid esters). Compounds in which R$^1$ is other than benzyloxycarbonyl and n is 2 (the β-alanyl derivatives) are also prepared by direct acylation using the appropriately substituted β-alanine acylating reagent. However, those compounds in which n is 1 or 3 and R$^1$ is other than CBZ, are not readily prepared by direct acylation but rather by acylation of the corresponding amino acid derivative, the glycyl or γ-butyryl ester derivative, obtained by hydrogenolysis of the corresponding CBZ ryanodine derivative, with the appropriate acylating agent.

In addition, benzyloxycarbonyl-β-alanyl-ryanodine (n=2) and its hydrogenolysis product, β-alanyl-ryanodine, likewise are useful in the preparation of compounds represented by the above formula in which Z is CH(CH$_3$) and in which n=2. Although, as mentioned above, such derivatives in which n=2 can be made by direct acylation of ryanodine, the hydrogenolysis route by way of β-alanyl-ryanodine is preferred when the preparation of such derivatives involves the incorporation of a radioactive or photo-activatable label.

The hydrogenolysis of $O_{10eq}$-CBZ-β-alanyl-ryanodine (Scheme I) is complex. Hydrogenolysis with a Pd catalyst under acidic conditions yields the anhydro derivative, $O_{10eq}$-β-alanyl-anhydro-ryanodinehydrochloride (V) which converts over time to the desired $10_{10eq}$-β-alanyl-ryanodine (V-II). Surprisingly, however, if the hydrogenolysis is carried out in the presence of base, triethyl amine for example, the hydrogenolysis proceeds smoothly in good yield to give $O_{10eq}$-β-alanyl-ryanodine (V-II) directly.

The preferred procedure for preparing the carbobenzyloxy derivatives comprehended by the above formula involves the use of a mixture of dicyclohexyl carbodiimide (DCC) and dimethylaminopyridine (DMAP) and is based on the procedure of Neises and Steglich, *Angew. Chem., Int, Ed. Eng.* 17 522 (1978).

Compounds of the second embodiment and represented by the above formula can be prepared from $O_{10eq}$-β-alanyl ryanodine or dehydroryanodine or from $O_{10eq}$-glycyl-ryanodine or dehydroryanodine by reaction with N,N'-di-Cbz-S-methyl-thiourea (see Nowak and Kania, *Rocz. Chem.* 43 1953 (1969)). The N,N'-bis-Cbz-guanidino-derivative thus prepared is converted to the desired unsubstituted guanidine derivative by hydrogenolysis, as by the use of 10% Pd/C in EtOH and Et$_3$N. These procedures are set forth in Scheme 2 below.

As with the compound of the first preferred embodiment, the preferred procedure for preparing the carbobenzyloxy derivatives of the second preferred embodiment and comprehended by the above formula involves the use of a mixture of dicyclohexyl carbodiimide (DCC) and dimethylaminopyridine (DMAP) and is based on the procedure of Neises and Steglich, *Angew. Chem., Int. Ed. Eng.* 17 522 (1978).

Another possible utility for the compounds of this second preferred embodiment of the invention arises from their high binding affinity for the ryanodine receptor. Such high binding affinity, for example of $O_{10eq}$-β-guanidinopropyl-ryanodine for the ryanodine receptor provides a feasible approach to the crystallization of the ryanodine receptor conjugate. (For other examples of the crystallization of membrane proteins, see Garavito and Picot, *J. Crystal Growth* 110 89 (1991), Luisi et al., *Nature* 352 497 (1991) and de Vos et al. *Science* 255 306 (1992)). A crystalline membrane protein-ryanodine complex thus produced could be subjected to x-ray crystal analysis to yield molecularly-detailed, direct evidence of the nature of the binding sites on the ryanodine receptor for the complexing ryanodine ester-ligand.

A third preferred embodiment of the invention provides novel N-(5-$^{125}$Iodo-4-azido-salicyloyl)-β-alanine derivatives having the general formula:

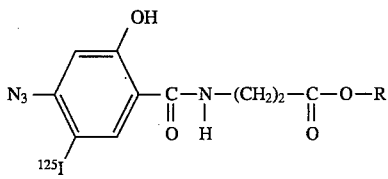

wherein R is —H or a lower alkyl (i.e. $C_1$ to $C_5$ alkyl) group.

The radio-labeled alanine derivatives of the third preferred embodiment and represented by the above formula can be prepared by reaction of N-hydroxy-succinimidyl-azido salicylic acid with a β-alanyl lower alkyl ester in the presence of a base such as a triethylamine, to form the N-(4-azido salicyloyl)-β-alanyl alkyl ester. The ester is radio-iodinated by reaction with Na$^{125}$I using the procedure of Mais et al., *J. Pharm. Exp. There.*, Vol. 235, No. 3, pp. 729–734 (1985). (Scheme III).

The radio-labeled alanine derivatives of the third embodiment are useful to radio-label other compounds which have amine, hydroxyl or sulfhydryl functions to create probes. For example the radio-iodinated alanine derivatives are useful to prepare radio-labeled ryanodine or dehydroryanodine derivatives from among those comprehended by the first and second embodiments discussed above. This is performed by coupling the radio-iodinated alanine derivative to a ryanodine or dehydroryanodine derivative having amine functionality or to ryanodine or dehydroryanodine directly.

This invention is further illustrated by the following specific examples.

SCHEME 1

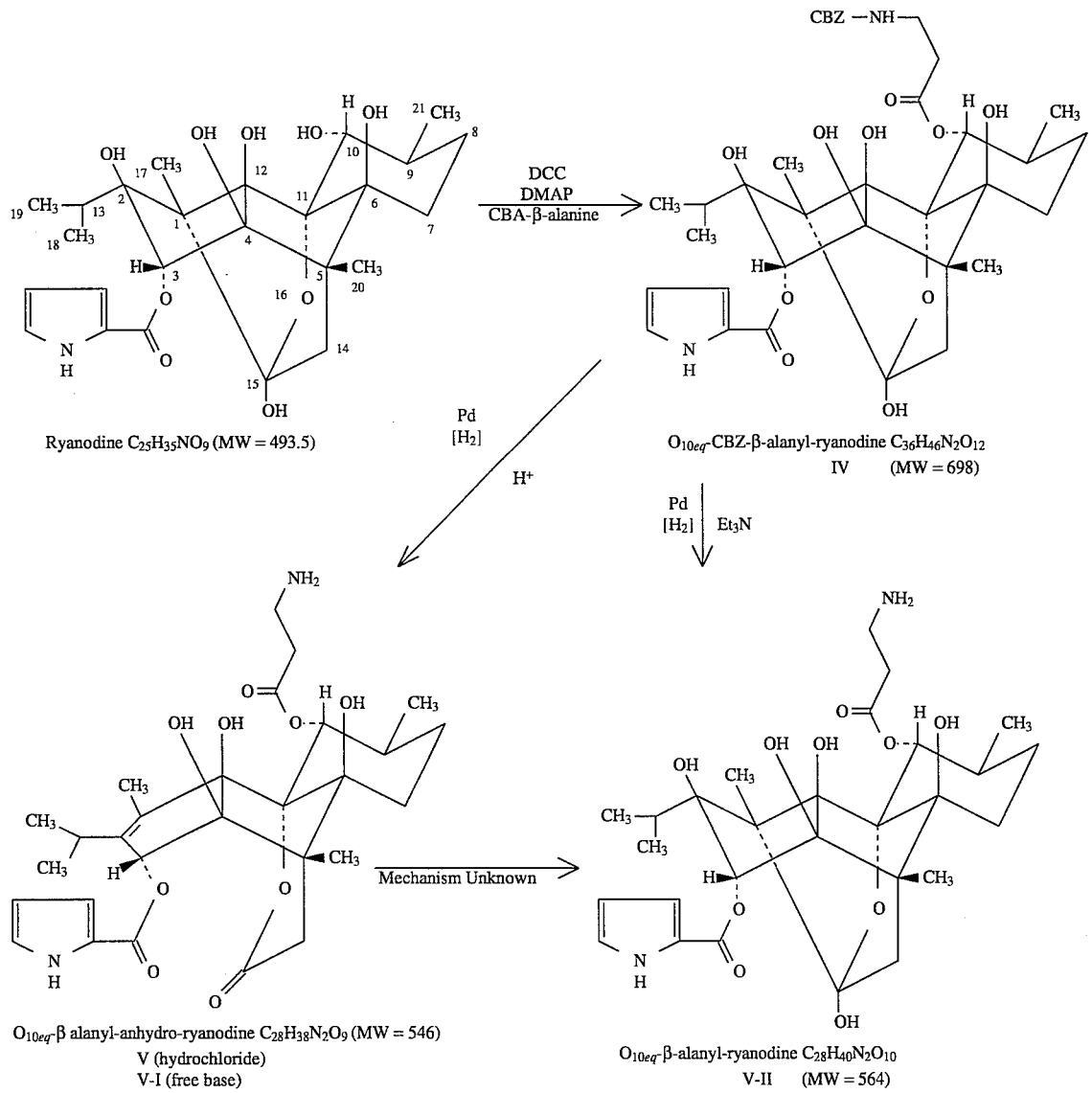

Scheme II: Semi-synthesis of $O_{10eq}$-Guanidino- and -Amino-acyl esters of Ryanodine
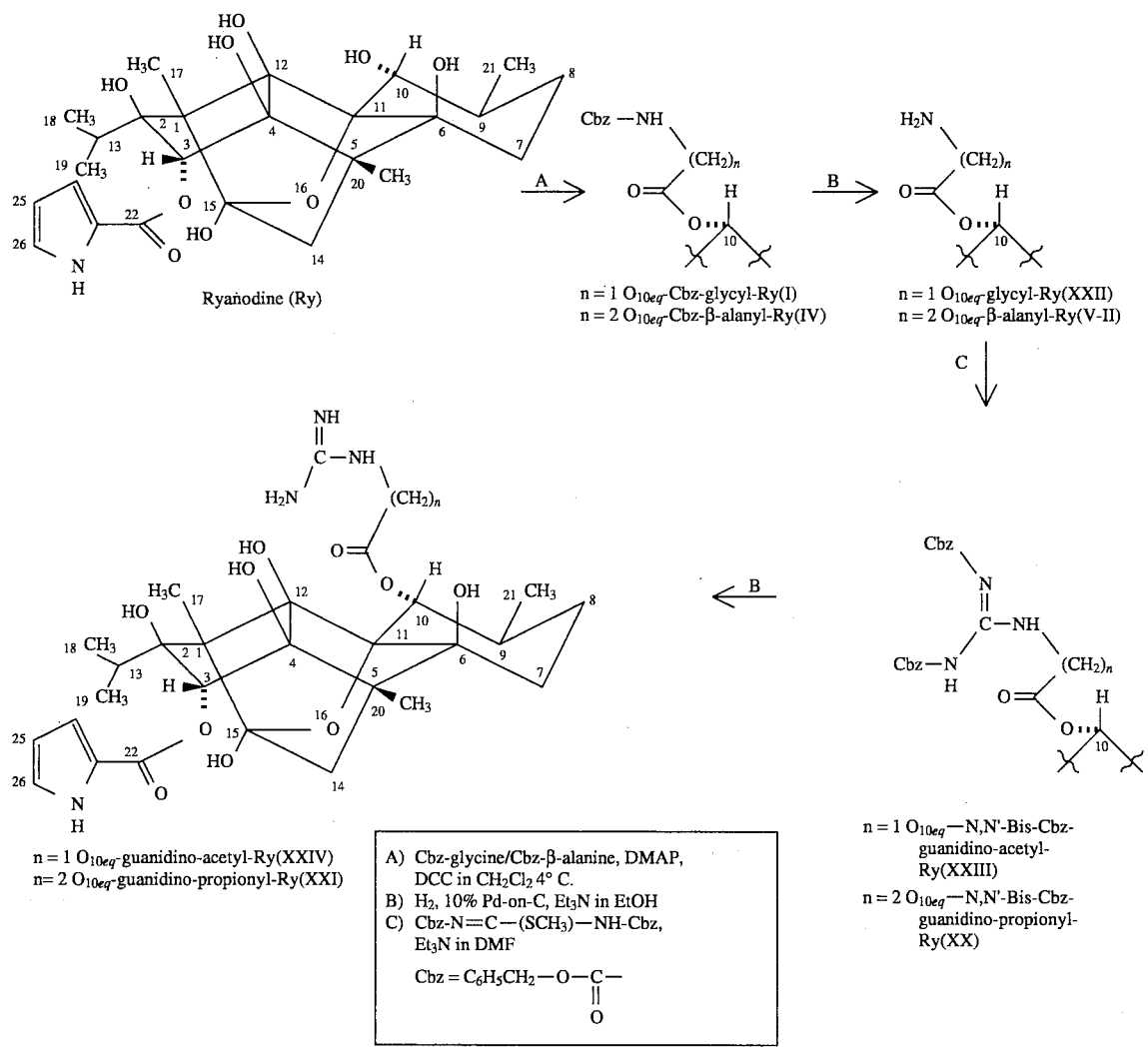

SCHEME III: Synthesis of $O_{10eq}$ N-(4-azido-5-$^{125}$Iodo salicyloyl)-β-alanyl -β-alanyl ryanodine starting from N-hydroxysuccinimidyl-4-azido salicylic acid.

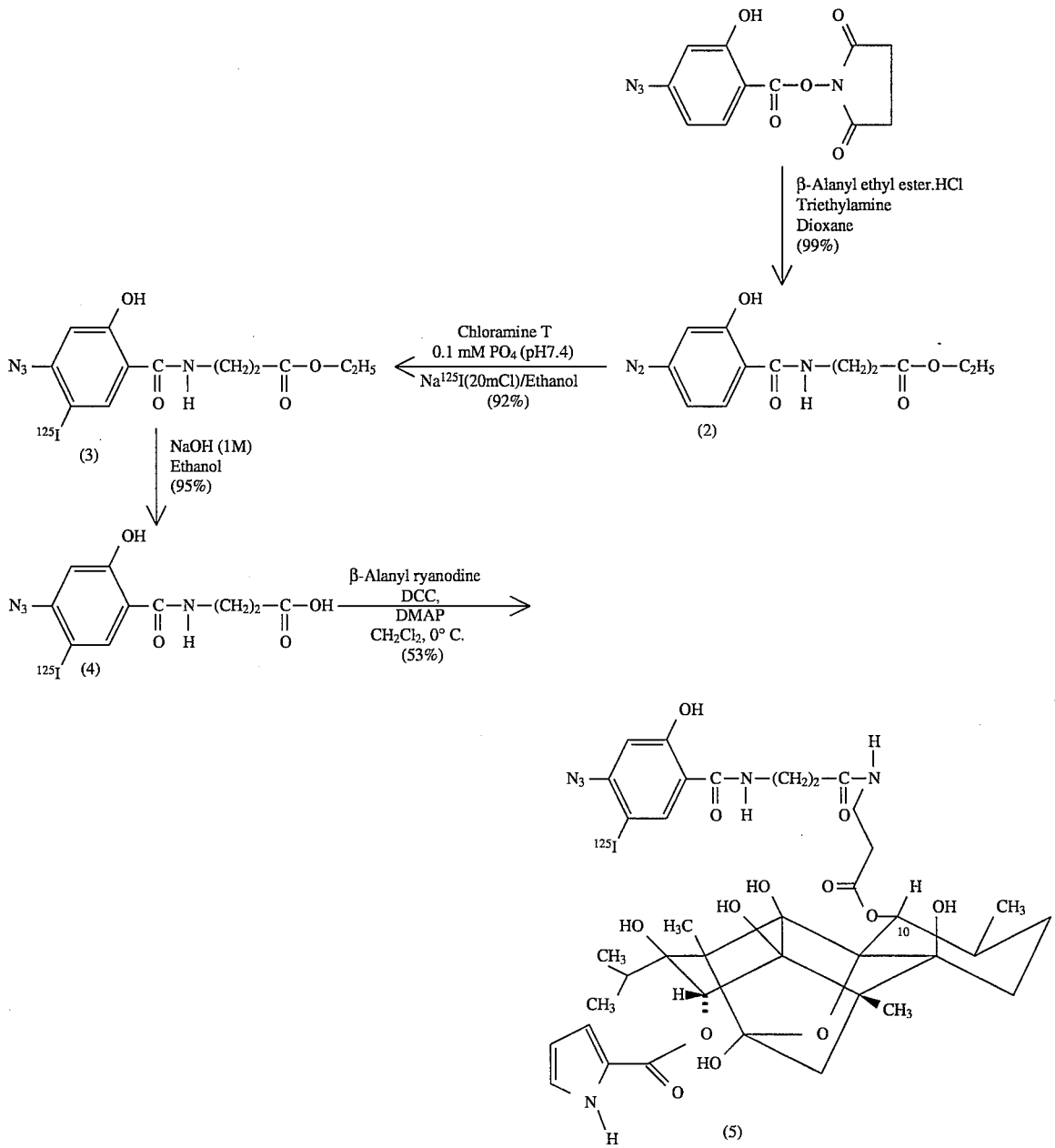

A(1). PREPARATIVE EXAMPLES OF FIRST PREFERRED EMBODIMENT

EXAMPLE 1

Preparation of $O_{10eq}$-[(N'Carbobenzyloxy)Glycyl]-Ryanodine(CBZ-glycyl-Ry)(I)

Dicyclohexylcarbodiimide (DCC, 154 mg., 0.75 mmol) was added at once to a 10 ml magnetically stirred solution of ryanodine (246.5 mg, 0.5 mmol), CBZ-glycine (Carbobenzyloxyglycine) (136 mg., 0.6 mmol), and dimethylaminopyridine (DMAP, 2.3 mg. 0.075 mmol, each dried in a vacuum desiccator over $P_2O_5$) in methylenechloride (dried 24 hours over Molecular Sieve).

After 30 min. the solution became turbid due to crystallization of dicyclohexylurea. An additional amount (40 mg.) of DCC was added and stirring continued for 3 hours. The solids (132 mg.) were filtered by gravity, washed with methylenechloride and discarded. The combined methylene chloride solutions (50 ml.) were washed first with 5 ml of iced 2N HCl solution to remove DMAP, then with 5 ml of iced 5% $NaHCO_3$ solution, filtered by gravity, and finally dried with anhydrous sodium sulfate.

Thin layer chromatography (TLC) using Silica Gel-backed plates (Merck Silica GEL 60, F-254 with 254 nm fluorescent indicator) with a chloroform: methanol: 40% aqueous methylamine solution (85:15:2, system A) revealed a major product (Rf=0.52) with traces of ryanodine (Rf=0.28) and of DMAP (Rf=0.6).

The dried methylenechloride solution (containing CBZ-glycyl-Ry, I) was concentrated under reduced pressure to a volume of 2 ml., applied to a chromatography column (inner diameter 9 mm) containing 24 g. Silica Gel (100–120 mesh). Elution proceeded first with chloroform, then with chloroform: methanol: 40%-methylamine (98:2:0.1) and, finally a 96:4:0.1 mixture of the same solvents. Fractions eluted with the latter system containing CBZ-gly-Ry were combined, the solvents removed under reduced pressure and the residue was taken up in 5 ml. of recently distilled dioxane. Lyophilization of the dioxane solution yielded the amorphous product (120 mg) which, upon digestion with n-pentane, yielded 90 mg. (26% of theory) of crystalline product (m.p. 182–184), Rf system A 0.52.

High Performance Liquid Chromatography (HPLC) was performed using a Waters $C_{18}$-microbondapak (4μ) Radial Pak liquid chromatography cartridge. The mobile phase used consisted of methanol-water mixtures in the following gradient protocol: 0–10 minutes 60% MeOH; 10–20 minutes 60–80% MeOH linear gradient; 20–30 minutes 80% MeOH. (Gradient Protocol A) Retention time CBZ-gly-Ry; 17.9 min.

Melting Point, 182°–184° C.

TLC Rf system A 0.52; HPLC retention time 17.9 min.

Mol. wt. found (HRMS by FAB, glycerol):$M^+ + Na^+$ = 707.3; $M^+ + NH_4^+$ = 702.3. Calcd. for $C_{35}H_{44}N_2O_{12}$:684.

U.V. λ=272, $\epsilon_{272}$=15,000

I.R.($CHCl_3$): 3700–3100(C—OH groups, pyrrole-NH and —OOCNH—), 1800–1600 shoulder at 1750 (esters- and carbamate—C=0), 1520(pyrrole) $cm^{-1}$.

$^1$H NMR ($CDCl_3$);7.25–7.35 (5 aromatic phenyl hydrogens), 6.95, 6.90, and 6.25 (three doublets for pyrrole hydrogens), 5.40(doublet, 10-H), 5.3 (s-3-H), 514 (s, phenyl—$CH_2$—O—), 2.50(d,—N—$CH_2$COO—), 2.33 (m, $C_{13}$—H), 0.84 (s,$C_{20}$—$H_3$).

**) Note: Most of the NMR bands in the spectrum of the ryanodine moiety of CBZ-Gly-Ry conform to those of ryanodine with one clear exception: the $C_{10}$-H band, which is present in ryanodine at 3.94 ppm, in the CBZ-Gly-Ry spectrum due to $C_{10}$-ester formation has shifted down-field and now appears in the CBZ-Gly-Ry Spectrum at 5.40 ppm.

EXAMPLE 2

Preparation of
$O_{10eq}$-(N-Benzoyl-β-alanyl)-Dehydroryanodine (II)

Following the above procedure., 100 mg. (0.2 mmol) of dehydroryanodine were reacted with 48 mg. (0.25 mmol) of N-benzoyl-β-alanine in the presence of DMAP and DCC to yield the compound of the title. The compound was isolated and purified also by the procedure of Example 1. 17 mg of the desired product were obtained having a TLC (system A) Rf 0.42 HPLC retention time (60% $CH_3OH$) 11.2 min. with shoulder at 12.4 min. Preparative HPLC purification using a Waters $C_{18}$microbondapak (10μ) Sep-Pak semi-preparative liquid chromatography cartridge was done with 60% methanol. Fractions containing II were combined, methanol was evaporated at temperatures below 50° C. under reduced pressure, and the aqueous solution freeze-dried to give 6 mg. of amorphous product (II) having the following characteristics:

TLC (system A) Rf=0.42 HPLC (gradient protocol A) retention time 9.9 min. *(New guard column)*.

IR($CHCl_3$): 3650–3150 (C—OH groups, pyrrole-NH, and —CONH—), 1550–1650(esters- and amide-C=0), 1520(pyrrole ring)$cm^{-1}$.

EXAMPLE 3

Preparation of
p-Iodobenzoyl-β-alanyl-dehydroryanodine (XII)

A solution of p-iodo-benzoylchloride (2.4 g, 10 mmol) in anhydrous pyridine (5 ml) was added to a stirred solution of β-alanyl ethyl ester hydrochloride (2 g, 13.5 mmol) in 20 ml of anhydrous pyridine. The reaction mixture was kept at room temperature for 18 hrs. with stirring. Pyridine was evaporated under reduced pressure and the residue was taken up in ethyl acetate. The ethyl acetate solution was washed first with 1N HCl, then with 1N NaOH solution and dried with anhydrous sodium sulfate. After evaporation of the solvent the residue was triturated with a mixture of pentane-ethyl ether (8:2), yielding 1.1 g. of N-(p-iodobenzoyl)-β-alanine ethyl ester, m.p. 94°–96° C.

This ester was hydrolyzed for 18 hours in a stirred mixture of 1N NaOH (12 ml) and ethanol (6 ml). Removal of the ethanol was followed by acidification with 6N HCl to pH=3–4 and extraction with ethyl acetate. Evaporation to small volume and cooling yielded 0.685 g. of the acid, N-(p-iodobenzoyl)-β-alanine, m.p. 166°–168° C.

Dehydroryanodine (100 mg, 0.2 mmol), N-(p-iodobenzoyl)-β-alanine (50 mg, 0.22 mmol) and DMAP (2 mg, 0.02 mmol), all dried over $P_2O_5$, were dissolved in a solvent mixture of $CH_2Cl_2$ (10 ml) and tetrahydrofuran (0.1 ml) dried over Molecular Sieve. To the stirred solution, dicyclohexylcarbodiimide (DCC, 52 mg., 0.25 mmol) was added at once and the stirred reaction maintained at room temperature for 6 hours. Water (0.1 ml) was added to inactivate excess DCC and stirring was continued for 30 minutes. The crystals of dicyclohexylurea thus formed were filtered off and washed twice with $CH_2Cl_2$.

The filtrate was evaporated under reduced pressure to small volume, the residue taken up in $CHCl_3$ and again evaporated to small volume. Crystals of dicyclohexylurea were filtered off, the filtrate was concentrated to a volume of 0.5–1 ml., and applied to the top of a column (6 mm inner diameter) containing 12 g. of Silica Gel suspended in $CHCl_3$. Elution of the product proceeded first with $CHCl_3$ (50 ml), then with mixtures (50 ml) of chloroform, methanol, and aq. 40% methyl amine (98:2:0.2, 96:4:0.4, and finally 94:6:0.6). Fractions eluted with the 96.:4:0.4 mixture containing the product (XII) were combined and the solvents removed under reduced pressure. The semi-solid residue was triturated with pentane-ethyl ether (8:2) and allowed to stand at room temperature for 4 hours. The white, crystalline product (XII), 12 mg, melts >220° C. dec.

TLC Rf (system A)=0.47. HPLC (60–80% $CH_3OH$) retention time=20.15 minutes.

Calculated for $C_{35}H_{41}IN_2O_{11}$ Mol. Wt. 792. HRMS, FAB, glycerol, LiI:799. $IC_{50}$(nM)=16.0. $K_D$(nM)=5.2.

The above compound (XII) is of interest in connection with the need for probes for the ryanodine binding site: since XII binds effectively to the ryanodine receptor, it serves as a model for radio-iodinated ligands. Such, more readily detectable $^{125}$I-ligands are effective probes for the detection of further ryanodine receptor sites in diverse tissues not readily detected with ryanodine itself.

Conversion of the derivative XII—and other suitable iodinated Ryanodine-ligand derivatives—to the radio-active species can be achieved using the radio-iodo-destannylation method [Blaszczak,. L. C., Halligan, N. G., and Seitz, D. E. *J. Labelled Compounds. Radiopharm.*, 27, 401 (1989); see also Mais, D. E., et al. ibid..29, 75–79 (1991) and *J. Med. Chem.* 34, 1511 (1991)]. See also Examples 22 and 23 for alternative methods for preparing radio-iodinated probes.

EXAMPLE 4

$O_{10eq}$-[N-(p-n-Butoxybenzoyl)-β-Alanyl]-Dehydroryanodine (XIII)

A solution of p-n-butoxybenzoylchloride (4.24 g., 20 mmol) in 5 ml of anhydrous pyridine was added to a stirred solution of β-alanine ethyl ester hydrochloride (4.6 g., 30 mmol) in 25 ml of anhydrous pyridine. The reaction mixture was kept at room temperature for 18 hours with stirring. Pyridine was evaporated under reduced pressure, and the residue was taken up in ethyl acetate. The ethyl acetate solution was washed first with. 1N HCl and then with 1N NaOH solution and dried with anhydrous sodium sulfate. After evaporation of the solvent the residue was triturated with a mixture of pentane and ethyl ether (9:1) yielding 4 g., of the white, crystalline product N-(p-n-butoxybenzoyl)-β-alanine ethyl ester, m.p. 86°–88° C.

This ester was hydrolyzed for 18 hours in a stirred mixture of 1N sodium hydroxide (15 ml.) and ethanol (10 ml.). Removal of the ethanol, was followed by acidification of the aqueous solution with 6N HCl to pH=2–4 and extraction with ethyl acetate yielded the acid N-(p-n-butoxybenzoyl)-β-alanine, 1.8 g., mp. 144°–146° C.

Dehydro-ryanodine (60 mg., 0.125 mmol), N-(p-n-butoxybenzoyl)-β-alanine (40 mg. 0.15 mmol) and DMAP (2 mg., 0.02 mmol), dried over $P_2O_5$, were dissolved in a solvent mixture of $CH_2Cl_2$(10 ml.) and tetrahydrofuran (0.1 ml) dried over Molecular Sieve. To the stirred solution dicyclohexylcarbodiimide (35 mg., 0.15 mmol) was added at once and the reaction mixture maintained at room temperature for 6 hours. Water (0.1 ml) was added and stirring continued for 30 minutes. The solids formed (dicyclohexylurea) were filtered and washed twice with $CH_2Cl_2$.

The combined filtrates were evaporated under reduced pressure to small volume, the residue taken up in $CHCl_3$ and again evaporated to small volume. Crystalis of dicyclohexylurea were filtered off and the filtrate concentrated to a volume of 1–2 ml.

This concentrated solution was applied to the top of a column (6 mm. inner diameter) containing 12 g. of silica gel suspended in chloroform. Elution proceeded first with chloroform (50 ml.), then with a mixture of chloroform/methanol, and 4% aq. methylamine (98:2:0.1); then this mixture (96:4:0.2). Fractions eluted with the latter mixture containing the product (XIII) were combined and the solvents removed under reduced pressure. The semi-solid residue was triturated with a pentanelethyl ether mixture (9:1) and allowed to stand at room temperature. A white crystalline product (XIII) was obtained, 4 mg., mp.p. 210°–220° C. (with dec). TLC Rf(system A)=0.56. HPLC (60–80% $CH_3OH$) retention time=24.0 min. Calculated for $C_{39}H_{50}N_2O_{12}$ Mol. Wt: 738. Mass spec. HRMS, FAB, glycerol with LiI: 745; $IC_{50}$(nM)=20.2; $K_D$(nM)=6.0

EXAMPLE 5

Preparation of $O_{10eq}$-[N-(1-Adamantanecarbonyl)-β-Alanyl]-Dehydroryanodine (III)

A. N-1-(Adamantanecarbonyl)β-alanine was prepared from 1-adamantanecarbonyl-chloride and β-alanine under modified Schotten-Bauman conditions as follows: A solution 1-adamantanecarbonyl-chloride (10 g., 0.05 mmol) in ether (5 ml.) was added to a vigorously stirred solution of β-alanine sodium salt (6.25 g., 0.055 mmol) and $NaHCO_3$ (5 g., 0.055 mmol) in 10 ml. of water. Stirring was continued for 18 hrs. The solution was acidified with iced concentrated hydrochloric acid, allowed to stand at room temperature for 1 hr. The precipitated solids—a mixture of 1-adamantanecarboxylic acid and the desired 1-adamantanecarbonyl-β-alanine—were filtered, dried in a vacuum desiccator over solid KOH, and then thoroughly digested with ether to remove 1-Adamantanecarboxylic acid. The remaining crystalline material was recrystallized from a chloroform-ether mixture (5:1). to yield 1.2 g. of N-(1-Adamantanecarbonyl)-β-alanine, m.p. 180°–182° C. having the following characteristics:

TLC using Silica Gel plates without fluorescent indicator Rf=0.8, using a chloroform:methanol:acetic acid mixture (85:15:3) and chlorine vapors for detection.

I.R.($CHCl_3$):3440(—CO$\underline{NH}$—), 1720(—$\underline{C}$OOH), and 1605 (—$\underline{C}$ONH—) $cm^{-1}$.

H-NMR($d_6$-DMSO); 7.0(q. —CO$\underline{NH}$), 3.05–2.75 and 2.1–1.8(2 m, —$CH_2CH_2$—) 1.6(s), 1.4(d), and 1.3(s) (adamantyl-9$\underline{H}$).

B. Dehydroryanodine (100 mg., 0.2 mmole), 1-adamantanecarbonyl-β-alanine (61 mg., 0.25 mmole) and 2 mg. of DMAP, each dried $P_2O_5$, were dissolved in 10 ml. of dried $CH_2Cl_2$. To the stirred solution was added 60 mg. (0.3 mmole) of DCC at once. Crystals of dicyclohexylurea appeared within ten minutes. After three hours the solids were filtered by gravity, washed with $CH_2Cl_2$; the combined organic layers were washed with 1N HCl, then with 5% $NaHCO_3$, and dried with anhydrous $Na_2SO_4$. The solvent was removed under reduced pressure to small volume (0.5 ml.) and applied to the top of a chromatography column (internal diameter 6 mm., 6 g. of Silica Gel,100–200 Mesh). Elution was effected with first chloroform, then chloroform:methanol:40 aq. methylamine (98:2:0.1). Fractions from the latter elution which contained the desired product (III) were combined and the solvents removed under reduced pressure. Lyophilization of the residue from recently distilled dioxane gave 32.5 mg. of amorphous product (III).

TLC Rf (system A) 0.49. HPLC (gradient protocol A) retention time 23.1 min.

$O_{10eq}$-β-alanyl-ryanodine (V-II) as obtained by hydrogenolysis of $O_{10eq}$-carbobenzyloxy-β-alanyl-ryanodine (IV) is a key intermediate to other derivatives as illustrated in Examples 10, 11, 16, 18 and 21 below.

EXAMPLE 6

Preparation of $O_{10eq.}$-Carbobenzyloxy-β-alanyl-ryanodine. (IV)

Ryanodine (150 mg., 0.3 mmol), CBZ-β-alanine(82.5 mg., 0.36 mmol), both dried by $P_2O_5$, and DMAP(2 mg.) were dissolved in $CH_2Cl_2$ (20 ml.) dried with Molecular Sieve. To the stirred solution dicyclohexylcarbodiimide(103 mg., 0.5 mmol) was added at once.

After 3 hrs. the product was obtained as described in Example 1, column chromatography (18 g. Silica Gel) using $CHCl_3$ and $CHCl_3:CH_3OH:40\%$ $CH_3NH_2$ mixture (98:2:0.2). Fractions containing IV were combined and solvents removed under reduced pressure. The residue yielded a crystalline product, IV, (44 mg.):m.p.=178°–180° C. TLC (system A) Rf=0.57. Analytical HPLC (gradient protocol A) retention time 19.2 min. U.V. λ max.=272 nm., $\epsilon_{272}$= 4,450. Mol.Formula Calcd. $C_{36}H_{46}N_2O_{12}$;(mol. wt. 698).

EXAMPLE 7

Alternate Preparation of $O_{10eq}$-CBZ-β-Alanyl-Ryanodine (IV)

Ryanodine (300 mg., 0.6 mmol), CBZ-β-alanine (160 mg., 0.7 mmol) and DMAP (7 mg., 0.07 mmol), dried over $P_2O_5$, were dissolved in a magnetically stirred mixture of $CH_2Cl_2$ (20 ml.) and tetrahydrofuran (0.2 ml.) dried with a Molecular Sieve. To the stirred solution dicyclohexylcarbodiimide (180 mg., 0.9 mmol) was added at once and the reaction was maintained at room temperature for 18 hrs.

Water (0.25 ml.) was added and stirring continued for 30 minutes. The solids formed (dicyclohexylurea) were filtered and washed twice with $CH_2Cl_2$. The filtrate was evaporated under reduced pressure to small volume, the residue taken up in $CHCl_3$ and again evaporated to small volume. Crystals of dicyclohexyl urea were filtered off, washed with $CHCl_3$, and the filtrate again concentrated to small volume (2–3 ml.).

This concentrated solution was applied to the top of a column (9 mm. inner diameter) containing 24 g. of Silica Gel in chloroform. Elution first proceeded with $CHCl_3$ (100 ml.), then with a mixture of $CHCl_3$, $CH_3OH$, and 40% aqu. methylamine solution (98:2:0.1), then this mixture (96:4:0.2), and finally (94:6:0.3). Fractions eluted with the (96:4:0.2) mixture containing the product (IV) were combined and the solvents removed under reduced pressure. The residue was redissolved in chloroform and the solvent removed under reduced pressure. The residue was triturated with a pentane:ethyl ether mixture (10:1, 10 ml.) and allowed to stand at 4° C. The white, crystalline product (IV), 150 mg. (36% of theoretical yield), melted at 178°–180° C.

TLC (system A) Rf=0.57. Analytical HPLC (60–80% $CH_3OH$) retention time 19.2 min. U.V., $\lambda_{max}$=272 nm., $\epsilon_{272}$= 14,450.

Mol. Formula. Calcd. $C_{36}H_{46}N_2O_{12}$;(mol.wt. 698). Mol.wt. (HRMS, FAB, Glycerol with LiI): $M^++Li^+$=705.3. $^1H$ nmr($CD_3OD$, δppm): 7.32(m, 5H,phenyl-aromatic protons),7.06, 6.87, 6.23(three double doublets for pyrrole hydrogens), 5.58(s, 1H, $\underline{H}$-C10), 5.07(d, 2H, Ar—$CH_2$—O), 3.45(t, 2H, —$NHC\underline{H}_2$—), 2.59(m, $\underline{H}$—C13), 1.40(s, C$\underline{H}_3$—Cl), 1.11(d, 3H, $C\underline{H}_3$—C13), 0.90(s, 3H, $C\underline{H}_3$—C5), 0.82(d, 3H $C\underline{H}_3$—C9), and 0.74(d, 3H, $C\underline{H}_3$—C13)

The above column chromatography fractions eluted with the (94:6:0.3) mixture containing unreacted ryanodine were collected. Solvent removal, followed by re-dissolving the residue in water, and freeze-drying, recovered 35 mg. (7%) of amorphous ryanodine.

EXAMPLE 8

$O_{10eq}$-β-Alanyl-Anhydroryanodine Hydrochloride (V), $O_{10eq}$-β-Alanyl-Anhydroryanodine (V-1) and $O_{10eq}$-β-Alanyl-Ryanodine (V-II)

Palladium on charcoal (10%, 15 mg.) was added to solution of $O_{10}$-CBZ-β-alanyl-ryanodine (IV, 285 mg., 0.42 mmol) in 50 ml. of ethanol containing 5 ml. (0.5 mmol) of aqueous 0.1 N HCl. The compound (IV) was hydrogenolysed under a hydrogen pressure of 50 lbs/in with continuous shaking for 3 hrs. The catalyst was filtered, ethanol was removed under reduced pressure and the residue diluted with 5 ml. of water. The clear aqueous solution was freeze-dried to yield 190 mg. of the light-tan hydrochloride (V).

TLC of V showed a single spot (system A) Rf=0.4. TLC ($CHCl_3$:$CH_3OH$, 85:15, system B) Rf=0.05. U.V. $\lambda_{max}$=272 nm; $\epsilon_{272}$=14,500.

Mol. Formula Calcd.. $C_{28}H_{38}N_2O_9$.HCl (Mol. wt. 546(+ 36.5).

Mass spectrum was run after three to four weeks of storage of the product at 4° C. At this time, a second product (V-II), Rf=0.22 (Rf=0.025 in system B) was present. The mass spectrum (FAB, Glycerol, with LiI) of this mixture (V, V-II) showed a peak $M^++Li^+$=571.3(564+7) and a peak at 553.3(546+7). Ryanodine itself when assayed (Li-technique) shows no dehydration ($M^+$–18) peak in the mass spectrum. A small peak is seen also at 705.3, corresponding to a residue of the precursor CZB-β-alanyl-ryanodine (Mol. Wt. 698).

The mixture of V and V-II hydrochlorides was separated by prior conversion to free-base ($Na_2CO_3$, $CHCl_3$) and chromatography on SILICAR using $CHCl_3$, and $CHCl_3$:$CH_3OH$ (2, 4 and 6%) with 5, 10, and 15 drops of $Et_3N$, respectively. Evaporation of fractions containing $O_{10eq}$-β-alanyl-anhydroryanodine (V-I, free base) and those containing $O_{10eq}$-β-alanyl-ryanodine (V-II, free base), and trituration of the respective residues after evaporation of solvents with a pentane-ether mixture (9:1) gave the respective crystalline products V-I, Rf=0.4 and V-II, Rf= 0.22, System A. Rf V-II 0.025 in System B. $IC_{50}$(nM)=4.2

Mass spec. the anhydro-product (V-I free base): HRMS (FAB, LiI) gave a peak $M^++Li^+$ at 553.2 (Calc. for $C_{28}H_{38}N_2O_9$=546).

V-I: $^1H$ nmr($CD_3OD$, δ ppm); 7.06, 6.87, 6.26 (three double doublets for pyrrole hydrogens), 6.15(q, 1H, $\underline{H}$C3), 5.63(d, 1H, $\underline{H}$C10), 3.42(d, $\underline{H}_b$) and 2.59(d, $\underline{H}_a$)(AB pattern, $H_2$C14), 2.71(m, 1H, $\underline{H}$C13), 3.07(t, 2H, —$C\underline{H}_2NH_2$), 2.61(t, 2H, —$C\underline{H}_2NH_2$), 2.61(t, 2H, —$C\underline{H}_2CO$—), 2.05(m, 1H, $\underline{H}$C9), 1.82(d, $C\underline{H}_3$—C1), 1.1(d, 3H, $C\underline{H}_3$—C13), 0.99(d, 3H, $C\underline{H}_3$—C9), 0.96(s, 3H, $C\underline{H}_3$—C5), 0.91(d, 3H, $C\underline{H}_3$—C13).

Mass. spec ($M^++Li^+$) of V-II, free base 571.3(564+ 7). Calculated for $C_{28}H_{40}N_2O_{10}$=564.

V-II: $^1H$-nmr ($CD_3OD$, δ ppm); 7.03, 6.87, and 6.23 (three double doublets for pyrrole-hydrogens), 5.58(s, 1H, $\underline{H}$C3), 5.4(d, 1H, $\underline{H}$C10), 3.0(t, 2H, —$C\underline{H}_2NH_2$), 2.60(t, 2H, —$C\underline{H}_2CO$—), 2.56(d, $\underline{H}_b$) and 1.94(d, $\underline{H}_a$) (AB pattern, $H_2$C14), 2.26(m, 1H, $\underline{H}$C13), 2.10(m, 1H, $\underline{H}$C9), 1.40(s, 3H, $C\underline{H}_3$—C1), 1.03(d, 3H, $C\underline{H}_3$—C13), 0.89(S, 3H, $C\underline{H}_3$—C5), 0.85(d, 3H, $C\underline{H}$—C9), and 0.74(d, 3H, $C\underline{H}_3$—C13).

EXAMPLE 9

Direct preparation of $O_{10eq}$-β-Alanyl-Ryanodine (V-II)

To a solution of CBZ-β-alanyl-ryanodine (IV, 112 mg., 0.16 mmol) in ethanol (25 ml.) containing 25 mg (0.25 mmol) of triethylamine was added 35 mg of 10% Palladium-on-Carbon.

The mixture was shaken under 40 lbs/in² of hydrogen pressure for one hour. Filtration to remove the catalyst and evaporation of the solvent under reduced pressure, yielded a residue which crystallized by trituration with a pentane-ethyl ether mixture (9:1); yield 37 mg. A second crop (7 mg.) was obtained by evaporation of the filtrate and freeze-drying the residue in dioxane. The product thus obtained consisted mainly of β-alanyl-Ry (V-II), some ryanodine (2–3%), and a small amount (1–2%) of D-alanyl-anhydro-ryanodine (V-I).

Chromatography over SILICAR gel. (20 g.) of 42 mg. of the above product using successively, $CHCl_3$—$CH_3OH$(98-2), then $CHCl_3$—$CH_3OH$—$Et_3N$(98-2-0.2), (96-4-0.4), (94-6-0.6) and (92-8-0.8) yielded 29 mg. of purified crystalline β-alanyl-ryanodine (V-II), m.p.=220°–230° C. (dec.)

TLC: Rf (system A)=0.22–0.24; Rf (System B)=0.025. HPLC (system B) retention time 8.8 min.

That the conversion of the anhydro-derivative (V) to the ryanodine derivative (V-II) would occur readily and spontaneously upon storage at refrigerator temperatures was unexpected in view of the difficult experience encountered in the conversion of synthetic anhydro-ryanodol to ryanodol in the classic work of Deslongchamps, Ruest et al. on "The total synthesis of (+)-ryanodol" Parts I, II, III and IV (*Can. J.Chem.*, 68, 115, 127, 153 and 187, 1990).

On the basis of the reported difficulty and obstacles encountered in the conversion of anhydro-ryanodol to ryanodol and in the conversion of anhydro-ryanodine to ryanodine by Professor Deslongchamps and co-workers in the above quoted publication Part IV, the facile, spontaneous conversion of D-alanyl-anhydro-ryanodine HCl (V) to β-alanyl-ryanodine (V-II) is most surprising indeed. The common identity of V-II as obtained by a) the spontaneous conversion of β-alanyl-anhydro-ryanodine HCl (V) upon storage at 4° C. for four weeks to V-II, and (b) the direct preparation of V-II by hydrogenolysis of CBZ-β-alanyl-Ry (IV) in the presence of triethylamine is evidenced by their identical behavior (a) on TLC(Rf=0.22 system A), (b) on HPLC (retention time 8.8 min., (50% $CH_3/H_2O$, 1% $Et_3N$), (c) in the N.M.R. spectrum, and—most significantly—(d) in the Receptor Binding Assay [$IC_{50}$(nM)=4.2 and 4.3, respectively].

As stated above, compounds according to FIG. 2 above in which n is 1 or 3 and $R^1$ is other than carbobenzyloxy or adamantyloxycarbonyl cannot be made in any satisfactory yield by a direct acylation of ryanodine or dehydroryanodine with the required esterifying moiety. These compounds, however, as well as the directly accessible derivatives in which n=2 when such are desired, carrying a photo- or radio-label, are readily accessible by direct acylation of the hydrogenolysis products $O_{10eq}$-glycyl-, $O_{10eq}$-γ-aminobutyryl-, and β-alanyl-ryanodine, respectively.

To illustrate this procedure, utilization of $O_{10eq}$-β-alanyl-ryanodine-(V-II), as obtained by hydrogenolysis of $O_{10eq}$-carbobenzyloxy-β-alanyl-ryanodine (IV), in acylation to provide various various molecular probes is described in Examples 10, 11, 16, 18 and 21 below.

EXAMPLE 10

Preparation of $O_{10eq}$-[N-(5-Azido-2-nitrobenzoyl)-β-Alanyl]Ryanodine (VI)

a) From β-Alanyl-Ryanodine (V-II)
5-Azido-2-nitrobenzoyloxysuccinimide (ANB-NOS, Pierce Chem. Co., 27 mg., 0.09 mmol) was added to a stirred solution of β-alanyl-ryanodine (v-II, 25 mg., 0.045 mmol) in freshly distilled dioxane (10 ml.) containing triethylamine (16 mg., 0.16 mmol). This and all subsequent operations were performed with exclusion of direct light. After 20 hrs. the clear, light-yellow solution was evaporated to dryness using a rotary evaporator. The residue was taken up in chloroform (1–2 ml.), and applied to the top of a chromatography column (internal diam. 15 mm.) containing SILICAR absorbent (20 g.) in chloroform. The product was eluted first with $CHCl_3$ (75 ml.) and followed by $CHCl_3$/$CH_3OH$/40% aqu. $CH_3NH_2$ mixtures: (98/2/0.2, 96/4/0.4, and 94/6/0.6). Fractions containing the desired product (VI) were combined and the solution evaporated to dryness under reduced pressure. The residue was dissolved in dioxane (5 ml.) and lyophilyzed to give the pale-yellow, photo-activatable product (VI), 10 mg.

TLC (System A) Rf=0.44. On the TLC plate the single spot of V-I turns yellow on exposure to U.V. light.

HPLC (Gradient system A) revealed a retention time of 12.3 min. The ultraviolet absorption spectrum of VI in methanolic solution shows the respective maxima at 272 and 320 nm. of its two chromophoric moieties (ryanodine, $\lambda_{max}$=320 nm) in a 1:1.05 molar ratio.

I.R. ($CHCl_3$): 3650(C—O$\underline{H}$, CON$\underline{H}$—, pyrrole-N$\underline{H}$), 2100(—$NO_2$), 2750(ester- and amide-C=O), 1518(aromatic pyrrole ring) $cm^{-1}$.

Calcd. for $C_{35}H_{42}N_6O_{13}$ Mol. Wt.: 754. Found HMRS-(FAB, glycerol, LiI): 761.

$IC_{50}$(nM)=36.6±2.8: $K_D$(nM)–12.5±1.0.

b) From β-Alanyl-anhydro-ryanodine Hydrochloride (V)
N-5-azido-2-nitrobenzoyloxysuccinimide (ANB-NOS Pierce Chem. Co.) 6 mg., 0.02 mmol was added to a stirred solution of β-alanyl-ryanodine HCl (V) 10 mg., 0.18 mmol in 10 ml of freshly distilled dioxane and triethylamine (4 mg., 0.04 mmol). This operation and all following steps were done essentially in the dark. After 18 hrs., the clear, light-brown solution was freeze-dried and the residue taken up in $CHCl_3$. The organic layer was washed with ice-cold 1N HCl, with 5% $NaHCO_3$ solution and dried over anhydrous $Na_2SO_4$. The chloroform solution was reduced to a small volume (0.4 ml.) and 4–6 ml of n-pentane were added. The resulting precipitate was gravity-filtered to yield a pale yellow photo-activatable product (VI, 9 mg.). TLC (System A) Rf=0.46. The spot for VI turns yellow on the TLC plate upon exposure to UV light. HPLC (gradient protocol A) retention time 12.3 min. The UV spectrum of VI in MeOH solution in equimolar concentrations shows the respective maxima at 272 and 320 nm. of its two chromophoric moieties (ryanodine $\lambda_{max}$=272; 5-azido-2-nitrobenzoic acid $\lambda_{max}$=320 nm.)

I.R. ($CHCL_3$:3650–3250 (C—OH groups; —CONH—, pyrrole-NH), 2100 ($N_3$), 2750 (esters- and amide C=O), 1518 (pyrrole ring) $cm^{-1}$.

The product (VI) obtained (a) from β-alanyl-ryanodine (V-II, free base), was in all respects identical to the product (VI) prepared (b) by the same, base-assisted procedure from β-alanyl-anhydro-ryanodine HCl (V). TLC (system A) Rf=0.46 and 0.44, respectively. When run together on the same plate the two samples of VI in this system ran with identical Rf=0.47.

The product (VI), prepared from V, in binding experiments to the ryanodine receptor revealed an affinity:

$IC_{50}$(nM)=37.2±9.7; $K_D$=14.0±3.6

This result compares favorably with the analogous values determined above for this product (VI) prepared from β-alanyl Ryanodine (V-II), namely:

$IC_{50}$(nM)=36.6±2.8; $K_D$(50)=12.5±1.0.

It is interesting to note that compound VI prepared from the anhydroryanodine-derivative (V) is the same as VI prepared from the ryanodine derivative (V-II). This finding is a second example of the conversion of an anhydro-ryanodine species to the corresponding ryanodine-derivative under the influence of mild base. In the first example—the conversion of β-alanyl-anhydro-ryanodine hydrochloride (V) to βalanyl-ryanodine (V-II) - this mild base function presumably is the primary amine of the $C_{10}$-β-alanyl side chain, while in the above preparation of the azido-nitro product (VI) from β-alanyl-anhydro-ryanodine HCl (V), triethylamine is present to act as a mild organic base. The above azido compound (VI) is photoactivatable and therefore can be used in photo-generation labelling studies to effect the covalent attachment of this ryanodine derivative (VI) to loci in, or adjacent to, the ryanodine receptor site. This photo-generated labelling procedure permits localization of the ryanodine binding site within the receptor molecule and determination of the detailed molecular architecture of the ryanodine binding site and its environs. A prerequisite for successful receptor structure determination is a satisfactory binding affinity or comparable biological quality of the photo-generation label, here compound VI. The demonstrated binding affinity of the azido-derivative (VI) is of a similar magnitude as that of ryanodine which fact further accentuates the usefulness of this derivative. The use of such photo-affinity labels in a related field-with the anticancer alkaloid, vinblastine—is described in papers by Nasioulas et al, *CAN. RES.* 50 403 (1990) and by Gambitter et al, *CAN. RES. & CLIN. ONCOL.* 109 Abs. Bio 06 (1985). See also, a chapter by Hagan Bayley "Photoregenerated Reagents in Biochemistry and Molecular Biology" appearing in *LABORATORY TECHNIQUES IN BIOCHEMISTRY AND MOLECULAR BIOLOGY*, Ed. Work and Burdon (Elsevier Amsterdam, New York and Oxford, 1983) for other types of labels that have been used with molecules of biological interest.

EXAMPLE 11

Preparation of $O_{10eq}$-N-BODIPY(FL C3)-β-Alanyl-Ryanodine (XV)

β-Alanyl-ryanodine (V-II, 5.6 mg, 0.01 mmol) dissolved in anhydrous dioxane (0.2 ml) was added to a magnetically stirred solution of 4,4-difluoro-5,7-dimethyl-4-bora-3a,4a-diaza-3-indacene-propionic acid N-hydroxy-succinimidyl ester (BODIPY FL-C3, MOLECULAR PROBES INC., 5 mg. 0.013 mmol) in anhydrous dioxane (0.8 ml) containing triethylamine (2 mg, 0.02 mmol). The reaction was maintained at room temperature for 16 hrs. and the solvent was then removed by freeze-drying. The semi-solid residue was taken up in $CHCl_3$ and the highly fluorescent solution was filtered. The residue obtained on evaporation of the solvent was applied to the top of a chromatography column (0.6 mm inner diameter)-containing 12 g. absorbent (SILICAR) in $CHCl_3$. The product was eluted with 50 ml portions of $CHCl_3/CH_3OH$, then with successive $CHCl_3/CH_3)OH/40\%$ aq. $CH_3NH_2$ amine mixtures 98:2:0.2, 96:4:0.4, respectively. Fractions of the latter two mixtures containing the product (XV) were combined and evaporated under reduced pressure to give a brown-red, semi-solid residue. Trituration with pentane-ethyl ether mixture (8:2) gave a red-brown crystalline product (2 mg). TLC revealed a major, single, fluorescent product, Rf (system A)=0.56.

The ultraviolet/visible light absorption measured in methanol revealed maxima of the ryanodine-moiety ($\epsilon$=8.000 at $\lambda$=272 nM) and the BODIPY moiety ($\epsilon$=72.000 at $\lambda$=530 nM), respectively, in a molar ratio of 1:1.2.

Calcd. for $C_{42}H_{54}BF_2N_4O_{11}$ Mol Wt. 838. HRMS (FAB, glycerol, LiI): 845.

$IC_{50}(nM)=41.2\pm2.7$; $K_D(nM)=15.8\pm1.0$

The above BODIPY Ryanodine fluorescent agent (XV) is useful in localization by microscopy of tissue ryanodine binding sites.

EXAMPLE 12

Preparation of $O_{10eq}$-N-(7-Amino-4-methylcoumarin-3-acetyl)-β-Alanyl-Ryanodine (XVI)

This fluorescent ryanodine derivative is prepared in a manner analogous to the preparation of the BODIPY-derivative (XV)—EXAMPLE 11—from β-alanyl-ryanodine (V) and the N-Hydroxy-succinimidyl 7-amino-4-methylcoumarin-3-acetate reagent (AMCA-NHS, Pierce Chemical Co.) in dioxane solution. The desired product was present in the reaction mixture, but on the small scale of the reaction employed the presence of several by-products rendered the isolation of pure XVI impractical. TLC system A: Rf=0.71; system B Rf=0.18.

Calcd. for $C_{40}H_{49}N_3O_{13}$ Mol Wt 779.

EXAMPLE 13

Preparation of Dehydroryanodine-$O_{10eq}$-Hemi-succinate (XVII)

To a stirred solution of dehydroryanodine (250 mg., 0.5 mmol) and dimethylaminopyridine (DMAP, 180 mg., 1.5 mmol) in 10 ml. of tetrahydrofuran (dried over Molecular Sieve) succinic anhydride (150 mg., 1.5 mmol) was added and stirring continued for 3 hrs. A further 50 mg. of succinic anhydride was added at this time. After 24 hrs. water (0.5 ml.) was added and the solution stirred for ½ hr. Tetrahydrofuran was removed by distillation under reduced pressure at a water bath temperature not exceeding 45° C.

The remaining residue was dissolved in water (5 ml.), redistilled triethylamine (0.5 ml.) was added and the aqueous layer then extracted with chloroform (three portions of 5 ml.) to remove DMAP.

The aqueous layer was held under reduced pressure (hi. vac.) to remove excess triethylamine and then acidified by stirring with DOWEX-50 $H^+$ ion exchange resin which lowers the pH to pH <7. The filtrate from this resin suspension was passed through a 9 mm diam. column containing additional (4 g.) DOWEX-50 $H^+$ resin, followed by an additional 50 ml. of distilled water. The effluent aqueous solution, pH 2.8, containing the product (XVII), 8,000 Opt. Density units, was lyophilyzed to give 300 mg. of (XVII) still containing succinic acid.

TLC analysis (system A) shows the presence of E (Rf 0.1) with a small amount of an un-identified by-product Rf=0.15.

Preparative HPLC using a Waters 10μ $C_{18}$-Bondapak Prep-Pak semi-preparative column and elution with 50% methanol provided fractions of purified succinate (XVII). Removal of methanol by distillation under red pressure, freeze-drying of the remaining aqueous solution gave 30 mg. of amorphous product (XVII).

TLC (system A) Rf=0.1. HPLC ($CH_3OH:H_2O$:acetic acid; 50:50:0.5, system C) retention time=11.4 min. $^1$H-NMR and mass. spec. data are available and confirm the structure of XVII as dehydoryanodine-$O_{10eq}$-hemi-succinate. As in CBZ-glycyl-ryanodine the $\underline{H}C_{10}$-OH peak in the NMR. spectrum in $CD_3OD$) has moved from its position in dehydroryanodine at 5.04(m, 10-$H_{ax}$) down-field to 5.92.

U.V. and I.R. spectra compatible with structure XVII

Mol. Formula: $C_{29}H_{37}NO_{12}$, Mol. Wt. 591; Hrms ($M^+ + Na^+$)=614.

EXAMPLE 14

Preparation of N-Methyl-Dehydroryanodine-Succinamidate(XVIII)

To a magnetically stirred solution of purified dehydroryanodine hemi-succinate (XVII) from Example 11 (30 mg., 0.05mmol) in water was added methyl amine hydrochloride (6.7.mg., 0.2 mmol) in 2 ml of water, 1-(3-dimethylaminopropyl)-3-ethyl-carbodiimide hydrochloride (40 mg., 0.2 mmol) and N-hydroxysulfosuccinimide, Na salt (Pierce Chemical Co.) (11 mg., 0.05 mmol). The pH of the stirred solution (3–4) was adjusted dropwise to pH=5–6 with 0.1N NaOH or 0.1N HCl, as required. A slight turbidity initially present disappears gradually. After 2 hrs., a further sample of EDC (20 mg.) was added. The final pH=5.5 (after 18 hrs.). The pH is then adjusted to about 8.5 with 5% $NaHCO_3$ and the resulting solution extracted with chloroform (3×10 ml). The solvent is evaporated; the residue taken up in water and the aqueous solution freeze dried to yield 12 mg. of a white amorphous, powdery product (XVIII).

TLC(system A) Rf=0.43. HPLC (system C), retention time=10.6 min.

I.R.($CHCl_3$): 3650–3150 (C—OH groups, pyrrole-N$\underline{H}$, —CONH—), esters and amide-C=O) $c^{-1}$.

Mol. Formula: $C_{30}H_{40}N_2O_{11}$; Mol. Wt. 604.

EXAMPLE 15

AFFINITY CHROMATOGRAPHY REAGENTS

Coupling of Dehydroryanodine $O_{10eq}$-Hemi-succinate (XVII) to AH-Sepharose 4B for Use in Affinity Chromatography of Ryanodine Receptor The resin (AH-Sepharose 4B) is suspended in a phosphate-buffered aqueous solution of the hemi-succinate (XVII) containing catalytic amounts of N-Hydroxysulfosuccinimide sodium salt (S-NHS). A two to three fold excess of water-soluble carbodiimide (EDC) is added to the stirred solution while the pH is maintained at 5–6. After 18 hrs. the resin is washed extensively with distilled water and collected.

The substitution-rate percentage of the available amino groups covered through amide linkage by succinate (XVII) is determined by base hydrolysis and U.V. analysis at 272 nm. This substitution rate can be expressed as mmoles dehydroryanodine/mg. of dried resin and was found to be satisfactory for affinity chromatography studies.

In the above example, the procedure of Inui et al, *J. Biol. Chem.* 262 15637 (1987) was modified by using the ryanodine-linked affinity chromatography described above en lieu of the resin types used by the authors.

EXAMPLE 16

Preparation of $O_{10eq}$-N-Biotinyl-β-Alanyl-Ryanodine (XIV)

β-Alanyl-ryanodine (V-II, 28 mg., 0.05 mmol) dissolved in dry FMF (0.2 ml) was added to a stirred solution of N-hydrosuccinimido-biotin (ImmunoPure* NHS-Biotin, Pierce Chemical Co., 16 mg, 0.05 mmol) in DMF (dried over Molecular Sieve, 1.5 ml) containing triethylamine (5 mg., 0.05 mmol). The reaction mixture was allowed to remain at room temperature for 18 hrs. DMF was then evaporated under reduced pressure. The residue was treated with chloroform (3 ml). To the resulting suspension ethyl acetate (1 ml) was added, the suspension centrifuged, and the supernatant was removed. The white solid residue was treated with anhydrous ether (1 ml), centrifuged and the supernatant decanted. The residual powdery white solid (9 mg) was collected.

TLC ($CHCl_3$:DMF, 75:25) revealed a single product (RF= 0.3). Calcd. for $C_{38}H_{54}N_4O_{12}S$ Mol. Wt. 790.52; found (HRMS, FAB, glycerol, LiI): 797.4

$IC_{50}(nM)=65.1\pm3.5$; $K_D(nM)=24.9\pm1.4$

The structures of the product of Examples 11, 12 and 16 are given in FIG. 3 below.

Figure 3

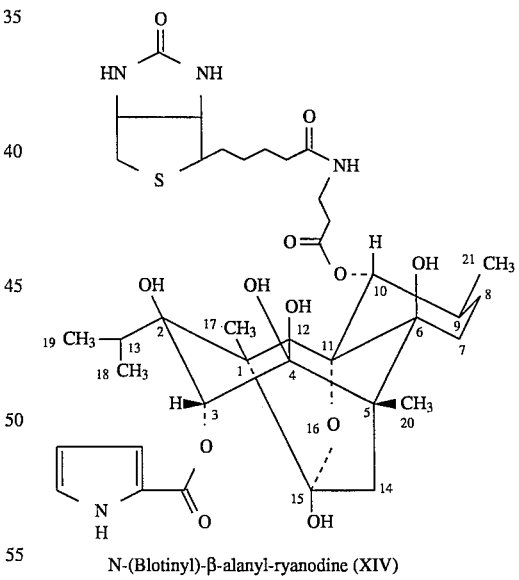

N-(Blotinyl)-β-alanyl-ryanodine (XIV)

-continued
Figure 3

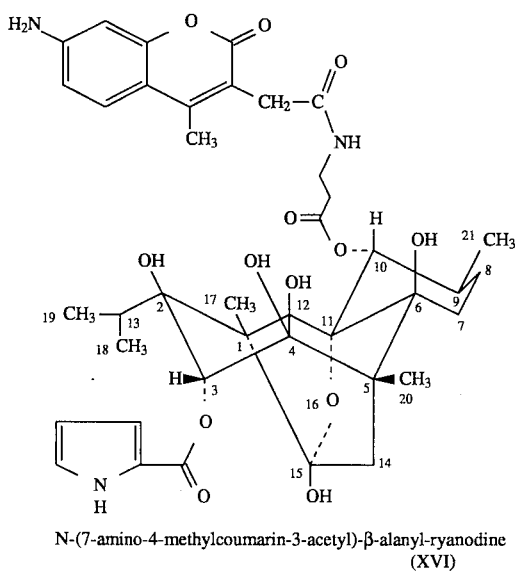

N-(7-amino-4-methylcoumarin-3-acetyl)-β-alanyl-ryanodine (XVI)

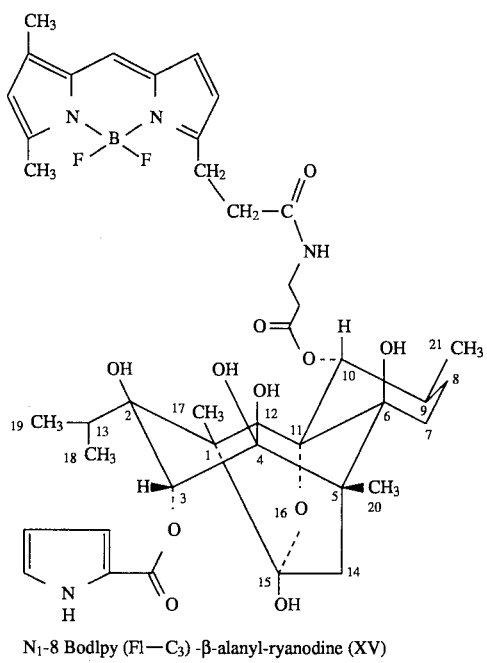

N$_1$-8 Bodlpy (Fl—C$_3$) -β-alanyl-ryanodine (XV)

EXAMPLE 17

COUPLING OF DEHYDRORYANODINE-O$_{10eq}$-HEMI-SUCCINATE (XVII) TO BSA TO SERVE AS AN ANTIGEN TO GENERATE "ANTI-RYANODINE" ANTIBODIES

A.) Dehydro-ryanodine succinate—BSA Conjugate Antigen (XIX)

To a stirred solution O$_{10eq}$-dehydoryanodine hemi-succinate (30 mg, 5.1 mmol), bovine serum albumin (BSA, 3.27 mmol), and N-hydroxy-sulfosuccinimide (NHS, 1.2 mg, 0.5 mmol) in phosphate buffer (10 ml 0.1M, pH=7.4) was added 1-(3,3-dimethylaminopropyl)-3-ethylcarbodiimide HCl (EDCI, 192 mg, 1 mmol) at once. The stirred reaction mixture was allowed to remain at room temperature for 2 hours and then at 4° C. for 16 hours. The solution was then transferred to dialysis tubing and dialyzed for 12 hour intervals first against 0.01M phosphate buffer, then against 0.001M phosphate buffer.

A total volume of 14.5 ml. of solution containing lysine-substituted BSA-dehydroryanodine-succinate conjugate (2.82 mg/ml) was obtained. Spectroscopic analysis of the solution—based on the molar absorption of dehydro-ryanodine (E=16,000) and the optical density (=0.694) of the (diluted) solution (47 ug/ml) relative to that of the corresponding unconjugated protein (BSA) control (=0.047)—showed that an average of 70% of the 56 lysine residues present per mole of BSA were substituted by dehydro-ryanodine-succinate.

B.) Antibodies against BSA-dehydro-ryanodine succinate antigen.

Serum samples (0.5 ml) were obtained from eight week old rabbits from an ear vein to serve as baseline. The rabbits were then injected intraperitoneally with BSA-dehydro-ryanodine succinate solution (0.5 ml). Two booster injections three weeks apart were given thereafter. Controls using corresponding concentrations of BSA were prepared concurrently.

Antibodies generated in the above immunization process against the BSA-dehydro-ryanodine succinate antigen were determined by the Enzyme Linked Immuno Sorbent Assay (ELISA) using 6% Fetal calf serum and anti-rabbit IgG peroxidase conjugate.

C.) Dhydro-ryanodine succinate—Keyhole Limpet Hemocyanin Antigen

This antigen was prepared—analogous to the above BSA-antigen—using Keyhole Limpet Hemocyanin in soluble from obtained from Pierce Chemical Co.

Spectroscopic analysis of the resulting solution (22.0 ml) containing KLH-dehydroryanodine succinate conjugate (4.54 mg/ml) revealed an optical density (0.230, 0.15 mg/ml relative to the control unconjugated KLH (0.140, 0.15 mg/ml).

The above conjugates of ryanodine and dehydro-ryanodine with bovine-serum albumin (BSA) and keyhole lympet hemocyanin (KLH) were prepared to serve as antigens for the generation of ryanodine antibodies. Ryanodine antibodies are of interest for the following purposes:

a) An immediate use for ryanodine antibodies is the development of a RADIOIMMUNO ASSAY(RIA) or ENZYME IMMUNO ASSAY (EIA) which would allow the detection of ryanodine at micro- and even nano-molar levels in biological fluids (serum) and/or in agricultural samples in areas where ryanodine-containing insecticide preparation are being used.

b) Ryanodine-antibodies would act as an antidote to treat animals or humans accidentally poisoned by an overdose of ryanodine.

c) Ryanodine-antibodies may serve as a tool to recognize, locate, and isolate (sequester) putative native peptido-mimetic biological agents involved in the physiological control of the mammalian ryanodine receptor.

d) Anti-iodiotypic antibodies would constitute a peptide model for and act as a peptido-mimetic of ryanodine.

The usefulness of these studies may be enhanced appreciably by the use of Ryanodine antibody-gold complexes.

While the affinity chromatography procedure for the isolation of Ryanodine receptor was illustrated by the use of dehydroryanodine-$O_{10eq}$-hemi-succinate (XVII), those skilled in the art will recognize that other compounds coming within the scope of this invention or their biotin-based equivalents would also be operable and even superior in procedures for the isolation of Ryanodine receptor.

In the use of the above Biotinyl-β-alanyl-Ryanodine (XIV) for recognition, separation, and isolation of the ryanodine receptor by affinity chromatography advantage is taken of the high affinity of the biotin moiety for avidin, e.g. in the form of avidin-linked microspheres.

In case difficulties are encountered in liberating ryanodine-moiety from the Avidin-Biotin-β-alanylryanodine-receptor complex, the use of a cleavable di-sulfide biotinylating reagent, NHS-SS-Biotin (Pierce Chemical Company) is envisaged.

A(2). PREPARATIVE EXAMPLES OF SECOND PREFERRED EMBODIMENT

EXAMPLE 18

Preparation of
$O_{10eq}$-β-Guanidinopropionyl-Ryanodine (XXI)

A solution of β-alanyl-ryanodine (V-II, 100 mg., 0.17 mmol) in 1 mL of stirred DMF containing 0.2 mmol $Et_3N$ was reacted with 200 mg (0.55 mmol) N,N'-bis-(Cbz)-S-methyl-isothiourea at ambient temperature for 18 hrs. The DMF was removed under reduced pressure (0.1 mm Hg) at 35° C. Column chromatography of the oily residue on SILICAR gel (system CMaM) yielded 100 mg. of $O_{10eq}$-β-N,N'-bis-Cbz-guanidino-propionyl-ryanodine (XX) having the following characteristics:

TLC(CMaM): Rf=0.72.

MS(FAB, LiI) $M^++7=881$.

Calcd. ($C_{45}H_{54}N_4O_{14}$): 874.

$^1$H-NMR ($CD_3OD$), δ ppm). Relevant peaks: 7.5–7.3(m, 10H, 2 φ-groups); 5.6(s, 1H, $\underline{H}$—C3); 5.35(d, 1H, $\underline{H}$-C10); 5.26(s, 2H, Ar—$C\underline{H}_2$—O—), 5.12(s, 2H, φ-C$\underline{H}_2$—O—); 3.72(m, 2H, —$C\underline{H}_2$NH); 2.70(m, 2H, —C$\underline{H}_2$CO—).

$IC_{50}$=43.6 nM. Single experiment

An ethanol solution of 75 mg. of 5a containing an equimolar amount of $Et_3N$ was shaken with 10% Pd/C under a hydrogen pressure of 40 lbs/in$^2$ for about 2 hrs. The catalyst was removed by filtration. Column chromatography using System CCaM gave 35 mg. of the compound (XXI) of the title having the following physical characteristics.

TLC (system BAWP; n-butanol/acetic acid/water/pyridine, 4/1/2/1) Rf=0.73

MS (FAB, LiI): $M^++1=607$.

Calcd. ($C_{29}H_{42}N_4O_{10}$): 606.

Anal. Calcd. C, 57.43; H, 6.93; N, 9.24. Found C, 51.78; H, 7.05; N, 8.29. Ratio C/N. Calcd. 6.22; found: 6.25.

$IC_{50}$=1.1+0.1 nM.

EXAMPLE 19

Preparation of $O_{10eq}$-Guanidinoacetyl-Ryanodine (XXIV)

Hydrogenolysis of $O_{10eq}$-Cbz-glycyl-ryanodine (Compound I of Example I) by the procedure of Example 18 yielded $O_{10eq}$-glycyl-ryanodine (XXII) having the following physical characteristics:

TLC(CMaM): Rf=0.23.

Calcd. for $C_{27}H_{38}N_2O_{10}$ Mol wt.=550. No phys.-chemical data available.

$IC_{50}$=1.8±0.2 nM.

Reaction of XXII with N,N'-bis-(Cbz)-S-methyl-isothiourea gave $O_{10eq}$-N,N'-bis-(Cbz)-guanidinoacetyl-ryanodine (XXIII) having the following physical characteristics: TLC(CMaM): Rf=0.6 $C_{44}H_{52}N_4O_{14}$ (mol. wt.=860); $IC_{50}$= 135.6 nM. Hydrogenolysis of this bis-(Cbz) derivative by the procedure of Example 18 gave $O_{10eq}$-guanidinoacetyl-ryanodine (XXIV) having the following physical characteristics:

TLC(BAWP); Rf=0.6; MS($C_{28}H_{44}N_4O_{10}$) (FAB, LiI): $M^+$ +1=593; Calcd. 592 (Mol. Wt.=550; $IC_{50}$=1.8+0.2 nM.

EXAMPLE 20

Preparation of
$O_{10eq}$-CBZ-β-Alanyl-Dehydroryanodine (XXV)

Dehydroryanodine (300 mg, 0.6 mmol), Cbz-β-alanine (210 mg, 0.9 mmol), dimethylaminopyridine (15 mg, 0.125 mmol) and dicyclohexylcarbodiimide (165 mg, 0.8 mmol), dried over phosphorus pentoxide, were mixed sequentially in methylene chloride ($CH_2Cl_2$) and allowed to react for 7 hours at 0° C. Water (3 ml) was added and stirring continued for 30 minutes. The solvents were then removed under reduced pressure and the residue dissolved in chloroform ($CHCl_3$, 3 ml). This solution was chromatographed on SILICAR gel (100 g), eluting sequentially with 150 ml each of $CHCl_3$/triethylamine (TEA) 100:1, $CHCl_3$/MeOH/TEA 96:4:1. The product of interest eluted with the 4% MeOH solvent mixture. On rotary evaporation and trituration of the residue with pentane 350 mg (82%) of the product (XXV) were obtained. TLC (system CMaM): Rf=0.55.

EXAMPLE 21

Preparation of $O_{10eq}$-β-Alanyl-Dehydroryanodine (XXVI)

The Cbz-product (XXV from Example 20) (25 mg, 0.035 mmol) was dissolved in absolute ethanol (12 ml) and hydrogenolysed in the presence of Palladium-on-Carbon (10%, 2.5 mg) under 40 psi hydrogen pressure for 55.minutes. The suspension was filtered and upon rotary evaporation and lyophilization from dioxane the product XXVI (15 mg, 75%) was obtained which in TLC (system CMaM) showed Rf=0.22.

β-Alanyl-dehydroryanodine (XXVI)—analagously β-alanyl-ryanodine (V-II, (5×, 8)—serves as the intermediate for the preparation of β-Guanidino-propionyl-dehydroryanodine (XXVII).

B(1) PHARMACOLOGIC FINDINGS FOR FIRST PREFERRED EMBODIMENT

The binding affinities of several compounds I-XVIII were determined in a traditional relative binding affinity assay (Table I). Briefly, skeletal sarcoplasmic reticulum membrane vesicles were incubated in the presence of 6.7 nM[$^3$H] ryanodine and increasing concentrations of the various unlabeled derivatives to competitively displace the [$^3$H]ryanodine. The $IC_{50}$ value for each derivative was determined from the appropriate displacement curve and compared to the IC$_{50}$ values for unlabeled ryanodine and dehydroryanodine.

Two of the compounds in Table 1 have been more extensively characterized pharmacologically. Both N'-methyl-dehydroryanodine-succinamidate (NMDS, XVIII) and CBZ-glycyl-ryanodine (I) exhibit pharmacology quite different from that of ryanodine and dehydroryanodine. Ryanodine (and dehydroryanodine, its pharmacologically equivalent natural congener) exhibits a complex pharmacologic profile. At low concentrations (<μM) ryanodine opens the SR Ca$^{++}$ release channel/ryanodine receptor, permitting an increased efflux of Ca$^{++}$ from the SR or from junctional SR Ca$^{++}$ vesicles. At higher concentrations of (>μM) ryanodine closes or inactivates the SR Ca$^{++}$ release channels interdicting Ca$^{++}$ accumulation by junctional SR vesicles. In contrast, neither XVII(NMDS)nor CBZ-glycyl-ryanodine (I) exhibits significant ability to close the channel at concentrations as high as 300 μM. However, both are only slightly less active than ryanodine for opening the channel. These data suggest that the addition of a side chain at the 10$_{eq}$-OH confers selective properties on the ryanodine derivatives. In addition, CBZ-glycyl-ryanodine (I) is more potent and more selective than XVIII(NMDS) suggesting that the electronic configuration of the carbamylfunction of the carbobenzyloxy function of (I) (and of IV) is more favorable for binding to the specific polar receptor binding site than the amide function of NMDS (XVIII).

The base-substituted ryanodine derivative, D-alanyl-ryanodine (v-II) in addition to being a highly useful intermediate for the synthesis of ryanodine molecular probes (e.g. VI, XIV, XV and XVI), binds 3.5–4 times stronger to the ryanodine receptor than does ryanodine itself. The product (V-II), O$_{10eq}$-β-alanyl-ryanodine is of great interest. It binds to the receptor with an affinity which is 4 times greater than that of ryanodine and is the first derivative with a receptor affinity higher than that of ryanodine itself.

IC$_{50}$(nM)=2.8±0.8; K$_D$(nM)=1.0.±0.27

Product (V-I), β-alanyl-anhydro-ryanodine, binds to the receptor with an affinity of 1/10 that of Ryanodine IC$_{50}$(nM)=106.0; K$_D$(nM)=37.0

Anhydro-Ryanodine itself binds to the receptor with an affinity of about 1% of the affinity of Ryanodine.

IC$_{50}$(nM)=>1,000; K$_D$(nM)=>350.

These observations suggest that addition of the β-alanyl side chain at C$_{10}$- is beneficial to ligand binding not only in the case of Ryanodine itself but also of anhydro-ryanodine.

This derivative (V-II) also displays pharmacological activity different from that of its parent, ryanodine. Studies of Ca$^{++}$ flux across sarcoplasmic membrane vesicles of both cardiac and skeletal muscle reveal that ryanodine has a biphasic effect on the receptor, the sarcoplasmic reticulum (SR) Ca$^{++}$ release channel. At low concentrations (<uM) ryanodine enhances Ca$^{++}$ flux across the SR membrane by opening the SR Ca$^{++}$ release channel but at higher concentrations (>uM) ryanodine inhibits Ca$^{++}$ flux by inactivating or closing the channel.

In contrast, β-alanyl-ryanodine (V-II), which binds with approximately four-fold higher affinity to the receptor, exhibits only the ability to enhance Ca$^{++}$ flux by opening the SR Ca$^{++}$ channel. The same selective activity of only opening this channel, albeit at higher dose levels than those of β-alanyl-ryanodine (V-II), is exhibited also by the O$_{10eq}$-aminoacyl derivatives CBZ-glycyl- (I) and CBZ-β-alanyl-ryanodine (IV).

It is, therefore, anticipated that this novel derivative (V-II) may appreciably facilitate an understanding of the mechanism of ryanodine-receptor interaction.

Table I gives the relative binding affinities for ryanodine, dehydroryanodine and O$_{10eq}$-ester derivatives thereof.

TABLE I

Relative Binding Affinities

| Name of O$_{10\ eq}$ Esters (I to XVIII) | IC$_{50}$ (nM) | K$_D$ (nM) |
|---|---|---|
| Ryanodine | 11.9 ± 1.6 | 4.4 ± 0.8 |
| Dehydroryanodine | 16.1 ± 4.1 | 5.4 ± 0.1 |
| CBZ-glycyl-Ryanodine (I) | 22.3 ± 7.3 | 6.6 ± 2.0 |
| Benzoyl-β-Alanyl-dehydro-Ryanodine (II) | 25.1 ± 8.2 | 8.2 ± 3.2 |
| Adamantoyl-β-Alanyl-dehydro-Ryanodine (III) | 72.8 ± 6.2 | 26.9 ± 3.6 |
| CBZ-β-Alanyl-Ryanodine (IV) | 12.3 ± 1.0 | 4.0 ± 0.2 |
| β-Alanyl-anydro-Ryanodine HCl (V) | 106.9 ± 19 | 37 |
| β-Alanyl-anhydro-Ryanodine (V-I) | 37 | NA |
| β-Alanyl-Ryanodine (V-II) | 2.8 ± 0.8 | 1.0 ± 0.3 |
| N-(5-azido-2-nitrobenzoyl)-β-Alanyl-Ryanodine (VI) | 36.6 ± 2.8 | 12.5 ± 1.0 |
| N-(p-Iodobenzoyl)-β-Alanyl Dehydroryanodine (XII) | 16.0 | 5.2 |
| N-(p-n-Butoxybenzoyl)-β-Alanyl Dehydroryanodine (XIII) | 28.0 ± 6.6 | 9.7 ± 2.5 |
| N-Biotinyl)-β-Alanyl-Ryanodine (XIV) | 65.1 ± 5.5 | 24.9 ± 1.4 |
| N-[BODIPY(FL C3)]-β-Alanyl-Ryanodine (XV) | 41.2 ± 2.7 | 15.8 ± 1.0 |
| Dehydroryanodine-hemisuccinate (XVII) | >1000 nM | |
| N-Methyl-Dehydroryanodine-succinamidate (XVIII) | 49.4 ± 10.6 | 19.9 ± 5.8 |

In the Table, CBZ=benzyloxycarbonyl.

The above numbers are mean values of replicate determinations, ± standard deviation.

Compounds of this invention suitably modified are useful in assaying for ryanodine receptor in various tissue fluids. Accordingly, one of the groups represented by R or R$^1$ in FIG. 2 can be modified by substitution therein of a chromophore, of an isotopic atom ($^{13}$C for example) or by a radioatom (Radio-iodine or $^{14}$C for example), as will be apparent to those skilled in the art. A preferred label would involve the use of tritium-labelled β-alanine in one of the above synthetic procedures in which an alanyl derivative is prepared. All such labelled 10$_{eq}$ derivatives of ryanodine or of dehydroryanodine are part of this invention since all such would be useful in the affinity labelling of ryanodine receptor.

In order to assay for ryanodine receptor, a labelled ryanodine or dehydroryanodine derivatives is coupled with ryanodine receptor by adding the label-carrying derivative to a solution thought to contain ryanodine receptor, separating the coupled receptor and then assaying the material so obtained for the presence of the chromophore or isotope.

Dehydro-ryanodine succinate and ryanodine succinate can be coupled with various proteins to provide antigens which can in turn be used to provide ryanodine antibodies. The preparation of such conjugates is illustrated below.

B(2) PHARMACOLOGIC FINDINGS FOR SECOND PREFERRED EMBODIMENT

The relative binding affinities (RBA) of ryanodine, dehydroryanodine and the O$_{10eq}$ ester, Cbz ester, guanidino and Cbz guanidino derivatives of ryanodine (as prepared by the above procedures) as well as of ryanodine and dehydroryanodine were determined using the method described in B(1) above, except using more highly purified ryanodine and dehydroryanodine standards (compare, e.g. the respective $IC_{50}$ values for these standards in Tables I and II). A comparison of the relative binding affinities of the novel esters with that of ryanodine reveals a 3- to 6-fold enhanced affinity of the basic esters V-II, XXII, XXI, AND XXIV, a slightly enhanced affinity of the mono-Cbz-protected esters IV and I and a 7–20 fold lessened affinity of the bis-$Cb_z$ protected esters XX and XXIII. Table II below gives the RBA's for these compounds.

TABLE II

Relative Binding Affinity of Ryanoids and $O_{10\ eq}$-Ryanodine Esters for the Sarcoplasmic Reticular $Ca^{++}$-Release Channel)

| COMPOUND | $IC_{50}$ (nM) ± S.D. |
| --- | --- |
| Ryanodine (1) | 6.2 ± 0.4 |
| Dehydro-Ryanodine (2) | 8.9 ± 1.2 |
| $O_{10\ eq}$-Ryanodine esters | |
| Cbz-β-Alanyl (IV) | 5.9 |
| Cbz-Glycyl- (I) | 4.8 ± 0.6 |
| β-Alanyl- (V-II) | 2.6 ± 0.4 |
| Glycyl- (XXII) | 1.8 ± 0.4 |
| β-N,N'-bis-Cbz-Guanidinopropionyl (XX) | 43.6 |
| N,N'-bis-Cbz-Guanidinoacetyl- (XXIII) | 135.6 |
| β-Guanidinopropionyl- (XXI) | 1.1 ± 0.1 |
| Guanidinoacetyl- (XXIV) | 1.8 ± 0.2 |
| β-Alanyl-anhydro-Ryanodin (V-I) | 149.0 |
| Anhydro-Ryanodine* | >1,000. |
| $O_{10\ eq}$-Dehydroryanodine esters | |
| Cbz-β-Alanyl- (XXV) | 4.43 |
| β-Alanyl- (XXVI) | 3.36 |

*J. MED. CHEM, 30 710 (1987).

To internally compare $IC_{50}$ values in Tables I and II, those in Table I can be adjusted to fit those in Table II by applying the ratio of the two ryanodine reference values, namely 6.2/11.9=0.52 to the respective value for compounds in Table I. For example, applying this ratio to the IC value of 12.3 nm for CBZ-β-alanyl-ryanodine (IV) in Table I, an adjusted value of 6.4 nm is achieved. This value substantially agrees with the value, $IC_{50}$=5.9 nM, listed for the same material in Table II.

Passive flux of $^{45}Ca^{2+}$ through the SR $Ca^{2+}$ release channel (see Besch et al. loc. cit. and Lattanzio et al., *J.B.C.* 262 2711 (1987)) was used to evaluate the ability of the basic ryanodine esters,. V-II and XXI, to open (activate) and close (deactivate) the channel. Briefly, junctional SR vesicles. from rabbit skeletal muscle were passively loaded with $^{45}Ca^{2+}$ in the presence and absence Of the esters. $Ca^{2+}$-efflux was then initiated by diluting the vesicles 100-fold into a low $Ca^{2+}$-concentration. $^{45}Ca^{2+}$ remaining in the vesicles was determined after a 3 sec. efflux period by termination and filtration of the vesicles followed by liquid scintillation counting.

An altered—unidirectional—pharmacological profile, differing from the biphasic profile of ryanodine, was observed for esters V-II and XXI.

Ryanodine exhibits two opposing effects on the sarcoplasmic reticular $Ca^{2+}$-release channel (SR CRC). Measuring the passive flux of $^{45}Ca^{2+}$ across the SR CRC (vide supra) allows quantitation of $Ca^{2+}$-efflux from skeletal SR vesicles as a means of assessing both opening and closing effects of ryanodine and its esters in a single assay. In this assay ryanodine activates the SR CRC at low μM concentrations, activation reaching its maximum at about 30 μM ryanodine, concentrations higher than 30 μM induce deactivation of the channel. The activation curve for the β-alanyl-ryanodine ester (V-II) is shifted to the left— toward lower concentrations—of that of ryanodine, maximal activation being reached at a concentration of 10 μM. This —three-fold—lowered shift parallels the two to three-fold greater RBA for this ester (V-II) (Table II).

A perhaps more significant aspect, however, of the interaction of the β-alanyl ester (V-II) with the receptor involves its overall effect on the channel. Whereas V-II, like ryanodine, induces full opening of the SR CRC, higher concentrations of V-II—up to 1 mM—exhibit none of the closing action seen with high concentrations of ryanodine. In preliminary experiments the guanidino-ester (XXI), which has an RBA for the ryanodine receptor about six times greater than that of ryanodine (Table II), also appears to be purely an activator of the SR CRC. Thus, while the base-substituted $O_{10eq}$-ryanodine esters (V-II, XXI) do retain the ability to open this channel, they entirely lack the ability of ryanodine to close the SR CRC. Whether the biphasic pharmacological activity pattern of parent ryanodine can be attributed a) to ryanodine interacting at two different, independent binding sites, b) to different conformations of the ryanodine molecule interacting at a single binding site, or c) to a combination of these (and perhaps other) factors are questions remaining to be answered in future studies. The selective channel activator action of the base substituted ryanodine esters V-II and XXI at the SR $Ca^{2+}$ release channel may well help to elucidate the mechanism of ryanodine's action.

C. PREPARATIVE EXAMPLES OF THIRD PREFERRED EMBODIMENT

Two methods were used to synthesize N-(4-azido-5-$^{125}$Iodo-salicyloyl)-β-alanyl-$O_{10eq}$β-alanyl ryanodine. These reactions were initially carried out using non-radio-labeled iodine and the reaction intermediates were confirmed by high resolution mass spectrometry. Infrared spectroscopy was used to indicate the presence of the azide functionality (2100 cm$^{-1}$). $^1$HNMR was used to identify the position of the iodine molecule in the aryl ring (two sharp singlets, 6.65 ppm, and 7.48 ppm strongly suggest that the iodine is in the 5 position on the aryl ring). All reactions were carried out under subdued light to minimize photo degradation.

EXAMPLE 22

Synthesis of
$O_{10eq}$-N-(4-azido-5-$^{125}$Iodo-salicyloyl)-β-alanyl-β-alanyl Ryanodine, From N-hydroxy-succinimidyl-azido Salicylic Acid Generally, four steps were required to obtain the desired product.

(a) N-(4-azido salicyloyl)-β-alanyl ethyl ester (AzSAEE) (XXVIII).

N-hydroxy-succinimidyl-4-azido salicylic acid (100 mg, 0.36 mmol) was dissolved in 15 mL anhydrous dioxane and the solution stirred. To this solution, β-alanyl ethyl ester HCl (62 mg, 0.41 mmol) was added followed by triethylamine (TEA, 0.5 mL, 0.4 mmol). The reagents were allowed to react for one hour at room temperature maintaining continuous stirring. The reaction solvent was removed under vacuum and the residue re-dissolved in chloroform ($CHCl_3$, 2 mL) and chromatographed using silica gel (18 g, mesh 100–200, Type 60A, Mallinkcrodt), eluting sequentially with 100 mL each $CHCl_3$/1% TEA, $CHCl_3$/1% methanol (MeOH)/1% TEA. The product of interest, XXVIII, began eluting with the tail end of $CHCl_3$ continued with the 1% MeOH. Total 100 mg (99%) of purified XXVIII was obtained, Rf=0.73 using $CHCl_3$/MeOH (85:15) as the developing solvent. A sharp peak at 2100 $cm^{-1}$ (Infrared spectroscopy) indicate the presence of the azido group.

(b) N-(4-azido-5-$^{125}$Iodo salicyloyl)-β-alanyl ethyl ester ($Az^{125}ISAEE$) (XXIX)

Iodination was performed using the procedure of Mais et al., *J. Pharm. Exp. There.*, Vol. 235, No. 3, pp. 729–734 (1985). XXVIII( 10.0 mg, 0.04 mmol) was dissolved in 2.0 mL absolute ethanol (Abs. EtOH) and the solution stirred. Sodium iodide (NaI, 6.75 mg, 0.045 mmol) and 200 μL $Na^{125}I$ (20 mCi in dilute sodium hydroxide) were added and the solution allowed to stir for an additional 2 minutes. Chloramine T (12.0 mg, 0.52 mmol in 1.5 mL 0.1M $PO_4$ buffer, pH 7.4, freshly prepared) was added as a bolus and the mixture stirred vigorously for 30 seconds. The reaction was terminated by the addition of 0.5 mL 5% sodium metabisulphite (freshly prepared). Distilled water (10 mL) was added to the mixture and the solution extracted with 6×15 mL $CHCl_3$. The pooled $CHCl_3$ extracts were dried over anhydrous sodium sulphate (anhy. $Na_2SO_4$), filtered and rotary evaporated to dryness. The residue was dissolved in dioxane (10 mL) and freeze dried. 13.4 mg (92%) of N-(4-azido-5-$^{125}$Iodo salicyloyl)-β-alanyl ethyl ester, $R_f$=0.56 ($CHCl_3$/MeOH, 85:15) was obtained.

(c) N-(4-azido-5-$^{125}$Iodo salicyloyl)-β-alanine ($Az^{125}ISA$) (XXX)

$Az^{125}ISAEE$ (XXIX) (13.4 mg, 0.033 mmol) was dissolved in 3 mL Abs. EtOH and allowed to stir for 10 hours. The following day, the mixture was acidified with 10 mL Hcl (pH 1.0) and the solution extracted with 6×15 mL $CHCl_3$. The pooled $CHCl_3$ fractions were dried over anhy. dioxane and freeze dried $Az^{125}ISA$ (XXX) (11.8 mg, 95%, was obtained, $R_f$=0.0 ($CHCl_3$/MeOH 85:15).

(d) $O_{10eq}$ N-(4-azido-5-$^{125}$Iodo salicyloyl)-β-alanyl-β-alanyl ryanodine ($Az^{125}IS$-βA-βAR) (XXXI)

$Az^{125}ISA$ (XXX) (11.8 mg, 0.032 mmol) was dissolved in anhy. $CH_2Cl_2$ (15 mL) and the solution stirred. $O_{10eq}$ β-alanyl ryanodine (V-II) (20.0 mg, 0.035 mmol), DMAP (4 mg, 0.04 mmol) and DCC (20 mg, 0.05 mmol) previously dried overnight over phosphorus pentoxide in vacuum were added sequentially and stirring contained for 7 hours at room temperature. The reaction was stopped by adding 1 mL water to the solution and stirring was continued for an additional 15 minutes. The solvents were then removed by rotary evaporation, the residue redissolved in 2 mL $CHCl_3$ and chromatographed using 10 g silica gel, eluting sequentially with 100 mL each $CHCl_3$/1% TEA, $CHCl_3$/2% MeOH/1% TEA, $CHCl_3$/4% MeOH/1% TEA, and $CHCl_3$/ 6% MeOH/1% TEA, respectively. The product, $O_{10eq}$ N-(4-azido-5-$^{125}$Iodo salicyloyl)-β-alanyl-β-alanyl ryanodine (XXXI) began eluting with 4% MeOH and upon freeze evaporation and freeze drying from dioxane, 17.5 mg (53%), $R_f$=0.30 ($CHCl_3$/MeOH/Aq. Methylamine, aq $MeNG_2$ 85:15:1) was obtained. Specific activity of $Az^{125}IS$-βA-βAR was 0.6 Ci/mMol, 11.2 mCi was incorporated into the probe.

EXAMPLE 23

Synthesis of $O_{10eq}$N-(4-azido-5-$^{125}$Iodo salicyloyl)-β-alanyl-β-alanyl Ryanodine ($Az^{125}IS$-βA-βAR) (XXXI) Starting From 4-amino Salicylic Acid Beginning with this reagent six reaction steps were required to obtain the desired product excluding the synthesis of $O_{10eq}$ β-alanyl ryanodine.

(a) N-hydroxy-succinimidyl-4-amino salicylic acid (HASA) (XXXII)

4-Amino salicylic acid (2.07 g, 13 mM), N-hydroxy-succinimide (2.07 g, 18 mmol) and DCC (3.44 g, 19 mmol), which had been dried over night over phosphorus pentoxide in vacuum, were dissolved sequentially in anhy. tetrahydrofuran (150 mL) in a round bottom flask. A vacuum was then applied for 30 seconds, the flask sealed and the reaction allowed to proceed for 7 hours at 1°–0° C., maintaining continuous stirring. After this time, the solvent was removed under vacuum and the residue re-dissolved in 15 mL $CHCl_3$/acetonitrile ($CH_3CN$) (98:2). This solution was chromatographed using 80 g silica gel, eluting sequentially with 300 mL each, $CHCl_3$/$CH_3CN$ (95:5), $CHCl_3$/$CH_3CN$ (90:10) and $CHCl_3$/$CH_3CN$ (50:50). HASA began eluting in the tail end of $CHCl_3$/$CH_3CN$ (95:5) and continued throughout the elution with 10% $CH_3CN$. A total of 2.4 g (70%) of purified HASA (XXXII) was obtained, $R_f$=0.64 ($CHCl_3$/$CH_3CN$, 20.3).

(b) N-(4-azido salicyloyl)-β-alanyl ethyl ester

HASA (XXXII) (1.0 g, 4 mmol) and β-alanyl ethyl ester HCl (0.76 g, 5 mmol) were dissolved in 75 mL dioxane. To this solution triethylamine (5 mL) was added and the resulting solution stirred for 2 hours at room temperature. At the end of the reaction, dioxane was rotary evaporated and the residue was redissolved in 12 mL $CHCl_3$. This solution was chromatographed using 50 g silica gel eluting with 300 mL each $CHCl_3$/1% TEA $CHCl_3$/1% MeOH/1% TEA and $CHCl_3$/2% MeOH/1% TEA, respectively. AS-β-AEE (XXXIII) began eluting with the tail end of $CHCl_3$ and continued throughout the elution with 1% MeOH. A 96% yield was obtained, $R_{f,s}$=0.54 and 0.50 in $CHCl_3$/MeOH/ aq.$MeNH_2$ (85:15:0.5) and $CHCl_3$/acetone (($CH_3$)$_2$CO) (20:5) respectively.

(c) N-(4-amino-5-$^{125}$Iodo salicyloyl)-β-alanyl ethyl ester ($A^{125}IS$-βAEE) (XXXIV).

AS-β-AEE (XXXIII) (10.0 mg, 0.033 mmol) was dissolved in 1.5 mL Abs. EtOH. To this solution, NaI (5.2 mg, 0.035 mmol) was added, followed by 100 μL $Na^{125}I$ (10 mCi) and stirring for 2 minutes. Chloramine T (8.0 gm, 0.035 mmol in 1 mL 0.1 M $PO_4$ buffer, pH 7.4, freshly prepared) was added as a bolus and the reaction allowed to proceed for 30 seconds ensuring vigorous stirring. The reaction was stopped by the addition of 0.3 mL 5% sodium metabisulphite. To the resulting solution, 10 mL distilled water was added and the mixture extracted with 5×15 mL $CHCl_3$, each time retaining the organic layer. The pooled $CHCl_3$ extracts were dried over anhy. $Na_2SO_4$, filtered and rotary evaporated to dryness. The residue was redissolved in 2 mL $CHCl_3$/1% TEA and $CHCl_3$/1.5% MeOH/1% TEA, respectively. $A^{125}IS$-β-AEE eluted with the 1.5% MeOH. Upon rotary evaporation and freeze-drying from dioxane, 13.2 mg (89.3%) $A^{125}IS$-β-AEE (XXXIV) was obtained, $R_f$=0.62 in $CHCl_3$/MeOH/aq.$MeNH_2$ (85:15:0.5).

(d) N-(4-amino-5-$^{125}$Iodo salicyloyl)-β-alanyl ($A^{125}IS$-βA) (XXXV)

$A^{125}IS$-βA-AEE (XXXIV) (13.2 mg, 0.031 mmol) was dissolved in 5.0 mL Abs. EtOH and to this solution, 1.0 mL of 1.0N NaOH was added. This suspension was stirred for 10 hours, followed by the addition of 10 mL HCl (pH 2). This solution was extracted with 5×15 ml $CHCl_3$. The pooled $CHCl_3$ layers were dried over anhy. $Na_2SO_4$ filtered and rotary evaporated to dryness. Upon freeze-drying from dioxane 11.5 mg (93%) of N-(4-amino-5-$^{125}$iodo salicyloyl)-β-alanine, $A^{125}IS$-βA (XXXV) was obtained, $R_f$=0.52 in $CHCl_3$/MeOH/formic acid (HCOOH) (85:15:0.5).

(e) N-(4-azido-5-$^{125}$Iodo salicyloyl)-β-alanyl ($A^{125}IS$-βA) (XXX)

The synthesis of N-(4-azido-5-$^{125}$Iodo salicyloyl)-β-alanine (XX) was performed using the procedure described by Ji et al., *J. Biol. Chem.*, Vol. 252, pp. 8524–8531 (1977). $A^{125}IS$-βA (XXXV) (11.5 mg, 0.029 mmol) was suspended in 5 mL cold conc. HCl in an ice/water bath. To this suspension, $NaNO_2$ (6.0 mg, 0.087 mmol in 1 mL cold distilled water) was added and the mixture stirred for 30 minutes. Sodium azide (10 mg, 0.15 mmol in 2 mL distilled water) was added very slowly (one drop/20 seconds) to the suspension maintaining continuous stirring and a reaction temperature of 0°–1° C. Stirring was continued for an additional 3 hours, at the end of which the solution was extracted with 4×15 mL $CHCl_3$. The pooled $CHCl_3$ extracts were dried over anhy. $Na_2SO_4$, filtered and rotary evaporated to dryness. The residue was redissolved in 2 mL $CHCl_3$ and chromatographed using 10 g silica gel, eluting sequentially with 100 mL each $CHCl_3$/1% HCOOH, $CHCl_3$/1% MeOH/1% HCOOH, $CHCl_3$/2% MeOH/1% HCOOH, and $CHCl_3$/4% MeOH/1% HCOOH. N-(4-azido-5-$^{125}$Iodo salicyloyl)-β-alanine, $Az_{125}IS$-βA, eluted in 4% MeOH. Upon rotary evaporation, redissolving in $CHCl_3$ and drying over anhy. $Na_2SO_4$, filtering evaporating to dryness, and freeze-drying from dioxane, 8.1 mg (67.8% of $Az^{125}IS$-βA (XXX), $R_f$=0.72 $CH_2Cl_2$/MeOH/HCOOH (85:15:1) was obtained.

(f) $O_{10eq}$ N-(4-azido-5-$^{125}$Iodo salicyloyl)-β-alanyl-β-alanyl ryanodine (AZ IS-βA-βAR) (XXXI)

$Az^{125}I$-βA (8.1 mg, 0.02 mmol) in dried $CH_2Cl_2$(4 mL) was added dropwise to a continuously stirred solution of $O_{10eq}$ β-alanyl ryanodine (20 mg, 0.035 mmol), DCC (20 mg, 0.052 mmol) and DMAP (2 mg, 0.018 mmol) in $CH_2Cl_2$ (10 mL). The reagents were allowed to react for 7 hours at the end of which 1 mL of distilled water was added and stirring continued for a further 30 minutes. The solvents were removed under vacuum and the residue redissolved in 2 mL $CHCl_3$/2% MeOH and chromatographed using 10 g silica gel, eluting with 100 mL each $CHCl_3$/1% TEA, $CHCl_3$/2% MeOH/1% TEA and $CHCl_3$/4% MeOH/1% TEA, respectively. The product $Az^{125}IS$-βA-βAR (XXXI) eluted with 4% MeOH and upon rotary evaporation an freeze-drying from dioxane, 6.1 mg (30%), $R_f$=0.29 ($CHCl_3$/ MeOH/aq. $MeNH_2$, 85:15:0.5) was obtained. Specific activity of $Az^{125}IS$-βA-βAR was 0.45 Ci/m Mol, 3.0 mCi was incorporated into the probe.

The relative binding of the non-radioactive $O_{10eq}$ N-(4-azido-5-$^{125}$Iodo salicyloyl)-β-alanyl-β-alanyl ryanodine ($Az^{125}IS$-βA-βAR) is $IC_{50}$=25.1±2.5×10$^{-9}$ M, $K_D$=8.8±1.6×10$^{-9}$M. In calcium flux experiments, even at concentrations greater than 1 mM this compound does not deactivate the CRC.

Using the above procedures, the following photo-activatable, radio-iodinated probes can be synthesized by coupling the inventive photo-activatable, radio-iodinated alanine derivative to ryanodine and dehydroryanodine derivatives described herein and to ryanodine and dehydroryanodine directly:

(a) $O_{10eq}$ N-(4-azido-5$^{125}$Iodo salicyloyl)-β-alanyl-glycyl ryanodine.
(b) $O_{10eq}$ N-(4-azido-5$^{125}$Iodo salicyloyl)-β-alanyl-glycyl dehydroryanodine.
(c) $O_{10eq}$ N-(4-azido-5$^{125}$Iodo salicyloyl)-β-alanyl-β-alanyl dehydroryanodine.
(d) $O_{10eq}$ Bis-N-(4-azido-5$^{125}$Iodo salicyloyl)-β-alanyl-guanidino acetyl ryanodine.
(e) $O_{10eq}$ Bis-N-(4-azido-5$^{125}$Iodo salicyloyl)-β-alanyl-guanidino acetyl dehydroryanodine.
(f) $O_{10eq}$ Bis-N-(4-azido-5$^{125}$Iodo salicyloyl)-β-alanyl-guanidino propionyl ryanodine.
(g) $O_{10eq}$ Bis N-(4-azido-5$^{125}$Iodo salicyloyl)-β-alanyl-β-guanidino propionyl dehydroryanodine.
(h) $O_{10eq}$ N-(4-azido-5$^{125}$Iodo salicyloyl)-β-alanyl-ryanodine.
(i) $O_{10eq}$-N-(4-azido-5$^{125}$Iodo salicyloyl)-β-alanyl-dehydroryanodine.

While the invention has been illustrated and described in detail in the figures and foregoing description, the same is to be considered as illustrative and not restrictive in character, it being understood that only the preferred embodiments have been shown and described and that all changes and modifications that come within the spirit of the invention are desired to be protected.

What is claimed is:

1. A compound of the formula

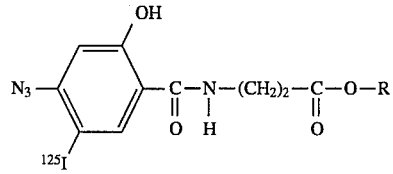

in which R is H or a lower alkyl group.

2. A compound according to claim 1 in which R is H.

3. A compound according to claim 1, in which R is lower alkyl.

* * * * *

UNITED STATES PATENT AND TRADEMARK OFFICE
CERTIFICATE OF CORRECTION

PATENT NO. : 5,510,500
DATED : April 23, 1996
INVENTOR(S) : Gerzon, Humerickhouse, Besch, Jr. and Bidasee It is certified that error appears in the above-indentified patent and that said Letters Patent is hereby corrected as shown below:

In col. 1, l. 61, please delete "confracture" and insert in lieu thereof --contracture--.

In col. 2, l. 45, please insert a space between the words "and" and "dehydroryanodine".

In col. 2, l. 60, please delete the period after the comma ".".

In col. 11, l. 51, please delete the period after "procedure".

In col. 13, l. 20, please delete the period after the first "with".

In col. 15, l. 2, please delete "4,450" and insert in lieu thereof --14,450--.

In col. 15, l. 65, please delete "lbs/in" and insert in lieu thereof --lbs/in$^2$--.

In col. 17, l. 3, please delete the "D" in "D-alanyl" and insert in lieu thereof the Greek symbol for "Beta".

In col. 17, l. 26, please delete the "D" in "D-alanyl" and insert in lieu thereof the Greek symbol for "Beta".

In col. 23, l. 48 (under the last drawing for Fig. 3), please delete "8" and insert in lieu thereof --[--. Please also insert --]-- after "$C_3$)".

In col. 25, l. 39, please delete "6" and insert in lieu thereof the Greek symbol for "delta".

In col. 27, l. 24, please delete "carbamyllfunction" and insert in lieu thereof --carbamyl-function--.

In col. 27, l. 29, please delete "v-II" and insert in lieu thereof --V-II--.

In col. 29, l. 40, please delete "IC" and insert in lieu thereof --$IC_{50}$--.

In col. 31, l. 41, please insert --)-- after "95%".

UNITED STATES PATENT AND TRADEMARK OFFICE
CERTIFICATE OF CORRECTION

PATENT NO. : 5,510,500
DATED : April 23, 1996
INVENTOR(S) : Gerzon, Humerickhouse, Besch, Jr. and Bidasee It is certified that error appears in the above-indentified patent and that said Letters Patent is hereby corrected as shown below:

In col. 32, l. 33, please insert as the rest of the title to subsection (b), --(AS-Beta-AEE) (XXXIII)--.

In col. 33, l. 46, please delete "AZ" and insert in lieu thereof --$AZ^{125}$--.

Signed and Sealed this

Fourth Day of November, 1997

BRUCE LEHMAN

*Attest:*

*Attesting Officer*  *Commissioner of Patents and Trademarks*